(12) United States Patent
Marczyk et al.

(10) Patent No.: US 7,845,533 B2
(45) Date of Patent: Dec. 7, 2010

(54) DETACHABLE BUTTRESS MATERIAL RETENTION SYSTEMS FOR USE WITH A SURGICAL STAPLING DEVICE

(75) Inventors: Stanislaw Marczyk, Stratford, CT (US); Megan Prommersberger, Wallingford, CT (US); Brian Nentwick, Greenfield Center, NY (US)

(73) Assignee: Tyco Healthcare Group LP, North Haven, CT (US)

( * ) Notice: Subject to any disclaimer, the term of this patent is extended or adjusted under 35 U.S.C. 154(b) by 607 days.

(21) Appl. No.: 11/821,330

(22) Filed: Jun. 22, 2007

(65) Prior Publication Data

US 2008/0314960 A1 Dec. 25, 2008

(51) Int. Cl.
*A61B 17/072* (2006.01)

(52) U.S. Cl. .................. 227/175.1; 227/19; 227/178.1; 227/179.1; 227/181.1

(58) Field of Classification Search .............. 227/175.1, 227/178.1, 19, 179.1, 181.1; 606/220
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 4,347,847 A | 9/1982 | Usher | |
| 4,354,628 A | 10/1982 | Green | |
| 4,452,245 A | 6/1984 | Usher | |
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,930,674 A | 6/1990 | Barak | |
| 5,002,551 A | 3/1991 | Linsky et al. | |
| 5,014,899 A | 5/1991 | Presty et al. | |
| 5,040,715 A | 8/1991 | Green et al. | |
| 5,065,929 A | 11/1991 | Schulze et al. | |
| 5,205,459 A | 4/1993 | Brinkerhoff et al. | |
| 5,263,629 A | 11/1993 | Trumbull et al. | |
| 5,314,471 A | 5/1994 | Brauker et al. | |
| 5,344,454 A | 9/1994 | Clarke et al. | |
| 5,392,979 A | 2/1995 | Green et al. | |
| 5,397,324 A | 3/1995 | Carroll et al. | |
| 5,425,745 A | 6/1995 | Green et al. | |
| 5,441,193 A | 8/1995 | Gravener | |
| 5,441,507 A | 8/1995 | Wilk et al. | |

(Continued)

FOREIGN PATENT DOCUMENTS

DE   1 99 24 311   11/2000

(Continued)

OTHER PUBLICATIONS

International Search Report from Application No. PCT/US2008/002981 dated Jun. 26, 2008.

(Continued)

*Primary Examiner*—Brian D Nash

(57) ABSTRACT

Systems of releasably connecting staple line buttress material to the jaws of a surgical stapling instrument are provided. The systems include retainers configured to engage the buttress material and releasably retain the buttress material on the jaws of the surgical stapling instrument prior to stapling tissue. In certain embodiments, the retainers remain with the jaws of the instrument after stapling of tissue. In alternative embodiments, the retainers remain with the buttress material after being stapled to tissue.

13 Claims, 17 Drawing Sheets

U.S. PATENT DOCUMENTS

| | | |
|---|---|---|
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 7,128,748 B2 | 10/2006 | Mooradian et al. |
| 2002/0016626 A1 | 2/2002 | DiMatteo et al. |
| 2002/0019187 A1 | 2/2002 | Carroll et al. |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0228446 A1 | 10/2005 | Mooradian et al. |
| 2005/0245965 A1 | 11/2005 | Orban et al. |
| 2006/0004407 A1 | 1/2006 | Hiles et al. |
| 2006/0085034 A1 | 4/2006 | Bettuchi |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0271104 A1 | 11/2006 | Viola et al. |
| 2007/0034669 A1 | 2/2007 | de la Torre et al. |
| 2007/0049953 A2 | 3/2007 | Shimoji et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2008/0029570 A1 | 2/2008 | Shelton et al. |
| 2008/0082126 A1 | 4/2008 | Murray et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |

FOREIGN PATENT DOCUMENTS

| | | |
|---|---|---|
| EP | 0 594 148 | 4/1994 |

| | | |
|---|---|---|
| EP | 1 520 525 | 4/2005 |
| EP | 1759640 A2 | 3/2007 |
| WO | WO 90/05489 | 5/1990 |
| WO | WO96/22055 A1 | 7/1996 |
| WO | WO 98/17180 | 4/1998 |
| WO | WO 99/45849 | 9/1999 |
| WO | WO 03/082126 A1 | 10/2003 |
| WO | WO 03/105698 A2 | 12/2003 |
| WO | WO 2006/023578 | 3/2006 |
| WO | WO 2006/044490 | 4/2006 |
| WO | WO 2006/083748 A1 | 8/2006 |
| WO | WO2008/057281 A2 | 5/2008 |

OTHER PUBLICATIONS

International Search Report from Application No. EP 08 25 1779 dated Jul. 23, 2008.
International Search Report from application EP 06016962.0 dated Jan. 3, 2007.
International Search Report from Application PCT/US05/36740 mailed Mar. 23, 2007.
European Search Report for EP 08252052.9-2310 date of completion is Mar. 11, 2010 (3 pages).

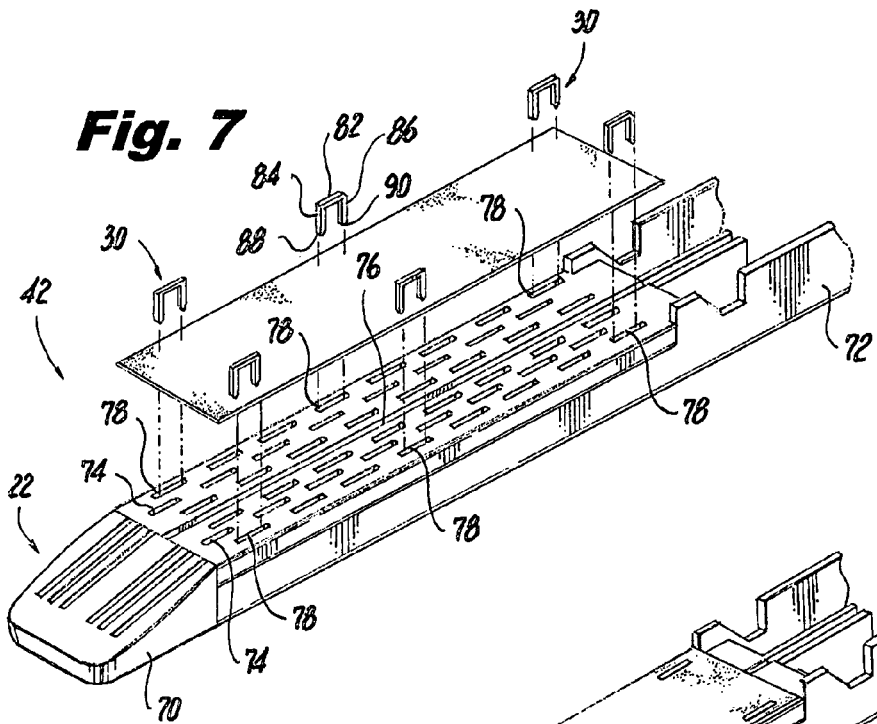
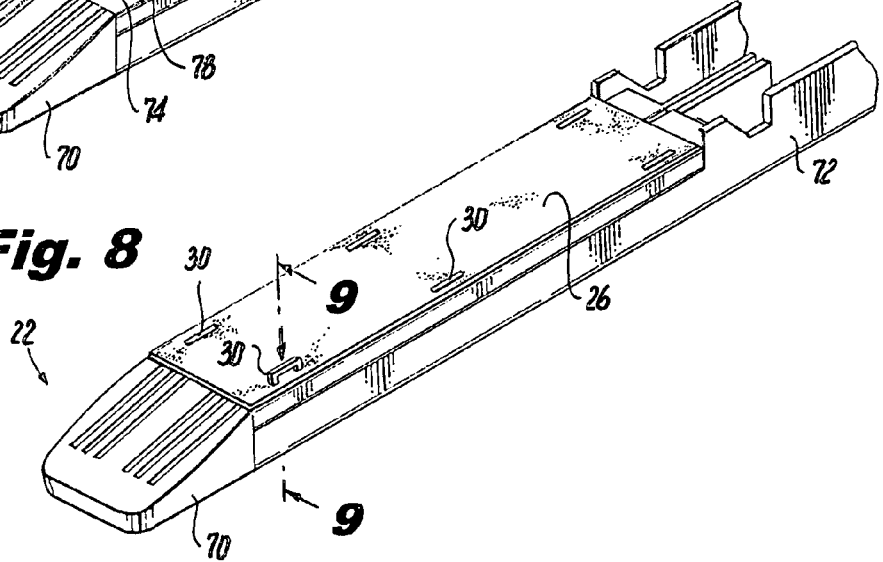
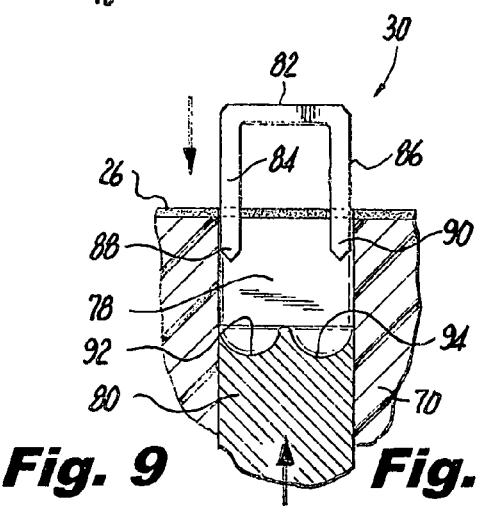
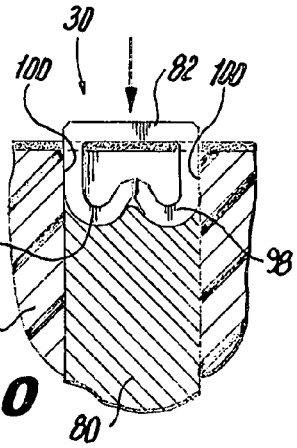

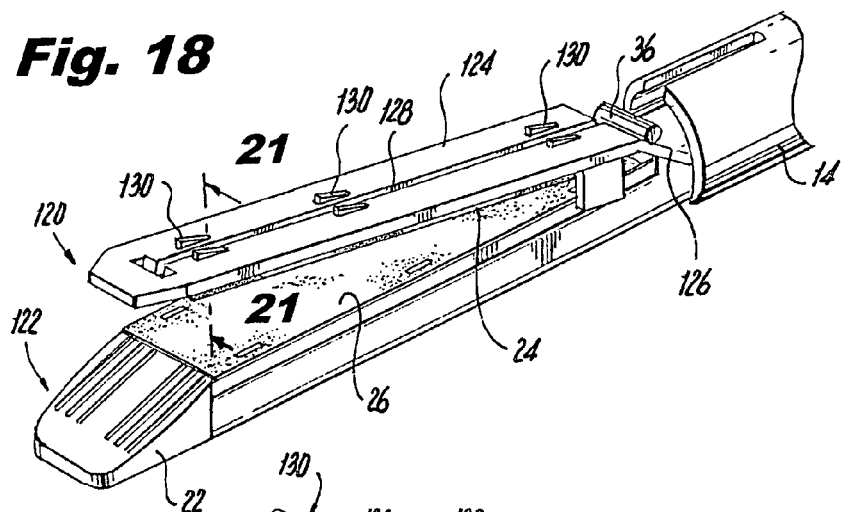
*Fig. 18*
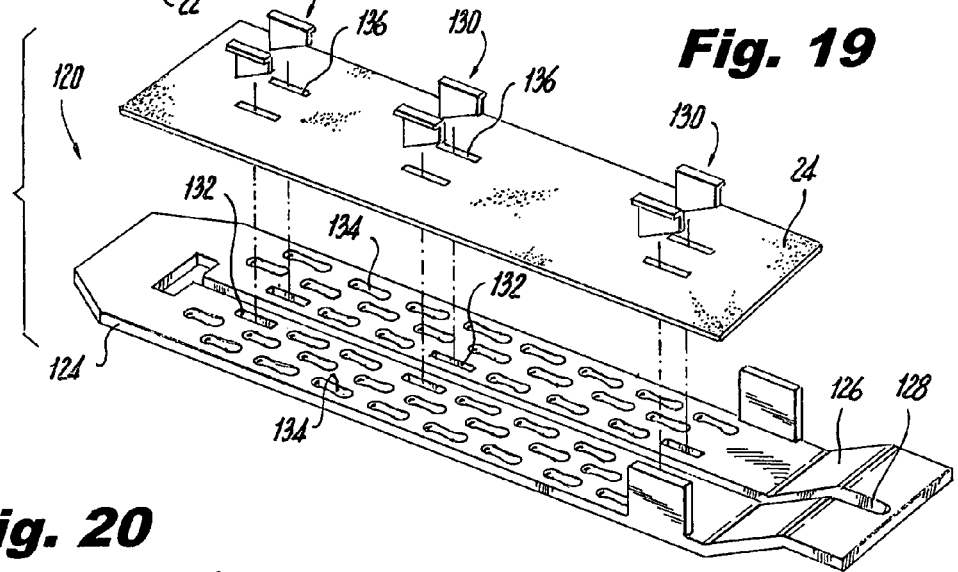
*Fig. 19*
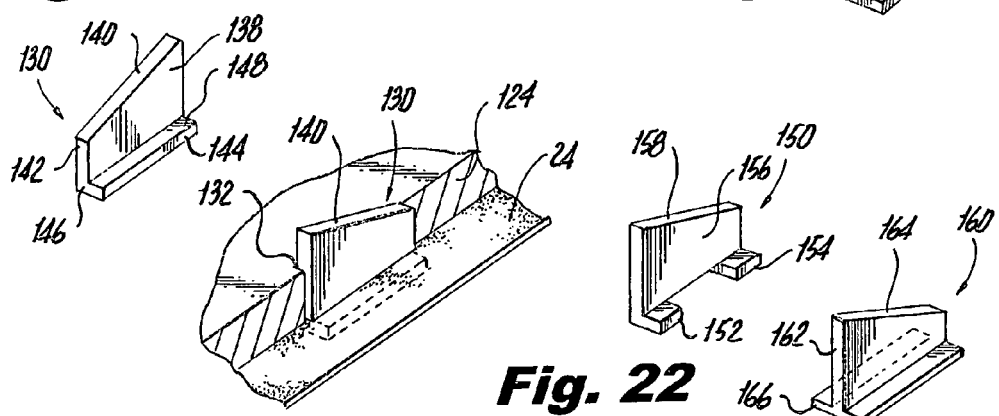
*Fig. 20*
*Fig. 21*
*Fig. 22*
*Fig. 23*

DETACHABLE BUTTRESS MATERIAL RETENTION SYSTEMS FOR USE WITH A SURGICAL STAPLING DEVICE

BACKGROUND

1. Technical Field

The present disclosure relates to attachment systems for staple line buttress materials. More particularly, the present disclosure relates to systems and methods of temporarily attaching staple line buttress materials to an anvil and staple containing cartridge of a surgical stapling instrument.

2. Background of Related Art

Surgical stapling instruments, or "stapling devices", are employed by surgeons to sequentially or simultaneously apply one or more rows of fasteners, e.g., staples or two-part fasteners, to body tissue for the purpose of joining segments of body tissue together. Such devices generally include a pair of jaws or finger-like structures between which the body tissue to be joined is placed. When the stapling device is actuated, or "fired", longitudinally moving firing bars contact staple drive members in one of the jaws. The staple drive members push the surgical staples through the body tissue and into an anvil in the opposite jaw which crimps the staples closed. If tissue is to be removed or separated, a knife blade can be provided in the jaws of the device to cut the tissue between the lines of staples.

When stapling relatively thin or fragile tissues, it is important to effectively seal the staple line against air or fluid leakage. Additionally, it is often necessary to reinforce the staple line against the tissue to prevent tears in the tissue or pulling of the staples through the tissue. One method of preventing tears or pull through involves the placement of a biocompatible fabric reinforcing material, or "buttress" material, between the staple and the underlying tissue. In this method, a layer of buttress material is placed against the tissue and the tissue is stapled in conventional manner. In more recent methods, the buttress material is positioned on the stapling instrument itself prior to stapling the tissue. An exemplary example of this is disclosed in U.S. Pat. No. 5,542,594 to McKean et al. In McKean et al., a tube of buttress material is slipped over the jaw of the stapler. The stapler is then actuated to staple the subject tissue and secure the buttress material between the tissue and staple line to reinforce the tissue and staple line.

When positioning the buttress material on the jaws of the surgical stapler, it is desirable to releasably retain the buttress material against the jaws. Thus, it is desirable to provide retainers for releasably retaining the buttress material against the jaws of the surgical instrument.

SUMMARY

There is disclosed a surgical stapler for deploying staples in tissue, the surgical stapler has a pair of jaws for engaging tissue, including a stapler cartridge and an anvil, where at least one of the jaws defines a plurality of recesses. A staple line buttress material is positioned on one of the jaws and a plurality of retainers pass through the staple line buttress material. Each of the retainers is disposed within one of the recesses in the jaws so as to releasably retain the staple line buttress material on the at least one jaw.

In one embodiment, the retainer is a staple having a backspan and a pair of legs extending from the backspan and the recesses in the at least one jaw defines a pair of holes, the legs of the staple pass through the holes such that tips of the legs are crimped over the staple line buttress material.

In another embodiment, the legs of the staple are inserted through the staple line buttress material such that the legs of the staple are partially positioned within the recesses and the backspan of the staple secures the staple line buttress material to the at least one jaw. In a more specific embodiment, the legs of the staple are crimped within the recesses.

In certain embodiments, the staple line buttress material includes a plurality of slots and the recesses are also formed as slots. The retainers are clips passing through the slots in the staple line buttress material and the jaw. In one embodiment, the retainer is a clip having an a plate and an angled lip extending from the plate, the angled lip engaging the staple line buttress material. The clip has an angled edge along one side, the angled edge being engagable with a driver of the surgical stapler.

In a further embodiment, the clip is an I-beam having a center portion and upper and lower beams extending from ends of the center portion. An underside of the upper beam engages the staple line buttress material and ends of the lower beam frictionally engage surfaces defining the recesses.

In certain embodiments, the retainer is absorbable within the body of a patient.

There is also disclosed a method of applying staple line buttress material to a surgical staple line. The method includes providing a surgical stapler having a pair of jaws including a staple containing cartridge and an anvil, the surgical stapler having a buttress material releasably disposed on at least one of the jaws and a plurality of retainers passing through the staple line buttress material and into recesses formed in the at least one jaw.

In the disclosed method the surgical stapler is actuated to drive staples contained in the staple containing cartridge through the buttress material and tissue captured between the jaws and into the anvil so as to staple the buttress material to the tissue. In one embodiment of the method, the retainers are retained within the at least one jaw after the buttress material has been stapled to the tissue. In an alternative embodiment of the disclosed method, the retainers are retained on the buttress material after the buttress material has been stapled to the tissue.

In one embodiment of the disclosed method the retainers are reverse staples frictionally retained within the recesses while in an alternative embodiment of the disclosed method the retainers are clips passing through the buttress material. A surface of the clips engage the buttress material.

DESCRIPTION OF THE DRAWINGS

Various embodiments of the presently disclosed systems for attaching staple line buttress materials to a surgical stapling instrument are disclosed herein with reference to the drawings, wherein:

FIG. 7 is a perspective view, with parts separated, of one embodiment of a staple cartridge and buttress material retention system;

FIG. 8 is a perspective view of a staple cartridge assembly illustrating the partially assembled staple cartridge buttress retention system;

FIG. 9 is a side view, partially shown in section, taken along line 9-9 of FIG. 8;

FIG. 10 is a side view, partially shown in section, similar to FIG. 9, illustrating crimping of a reverse staple of the staple cartridge buttress retention system;

FIG. 18 is an enlarged perspective view of the distal end of the surgical stapling instrument of FIG. 1 incorporating alternative embodiments of retention systems for attachment of staple line buttress materials to an anvil and staple cartridge;

FIG. 19 is a perspective view, with parts separated, of another embodiment of an anvil and buttress material retention system in accordance with FIG. 18;

FIG. 20 is a perspective view of a retention clip of the anvil buttress retention system of FIG. 19;

FIG. 21 is a perspective view, partially shown in section, taken along line 21-21 of FIG. 18;

FIG. 22 is a perspective view of an alternative retention clip for use in the anvil buttress retention system of FIG. 18;

FIG. 23 is a perspective view of a further alternative retention clip for use in the anvil buttress retention system of FIG. 18;

DETAILED DESCRIPTION OF EMBODIMENTS

Embodiments of the presently disclosed detachable buttress material retention systems for use with surgical stapling instruments will now be described in detail with reference to the drawings wherein like numerals designate identical or corresponding elements in each of the several views. As is common in the art, the term 'proximal" refers to that part or component closer to the user or operator, i.e. surgeon or physician, while the term "distal" refers to that part or component further away from the user.

Figure 1:
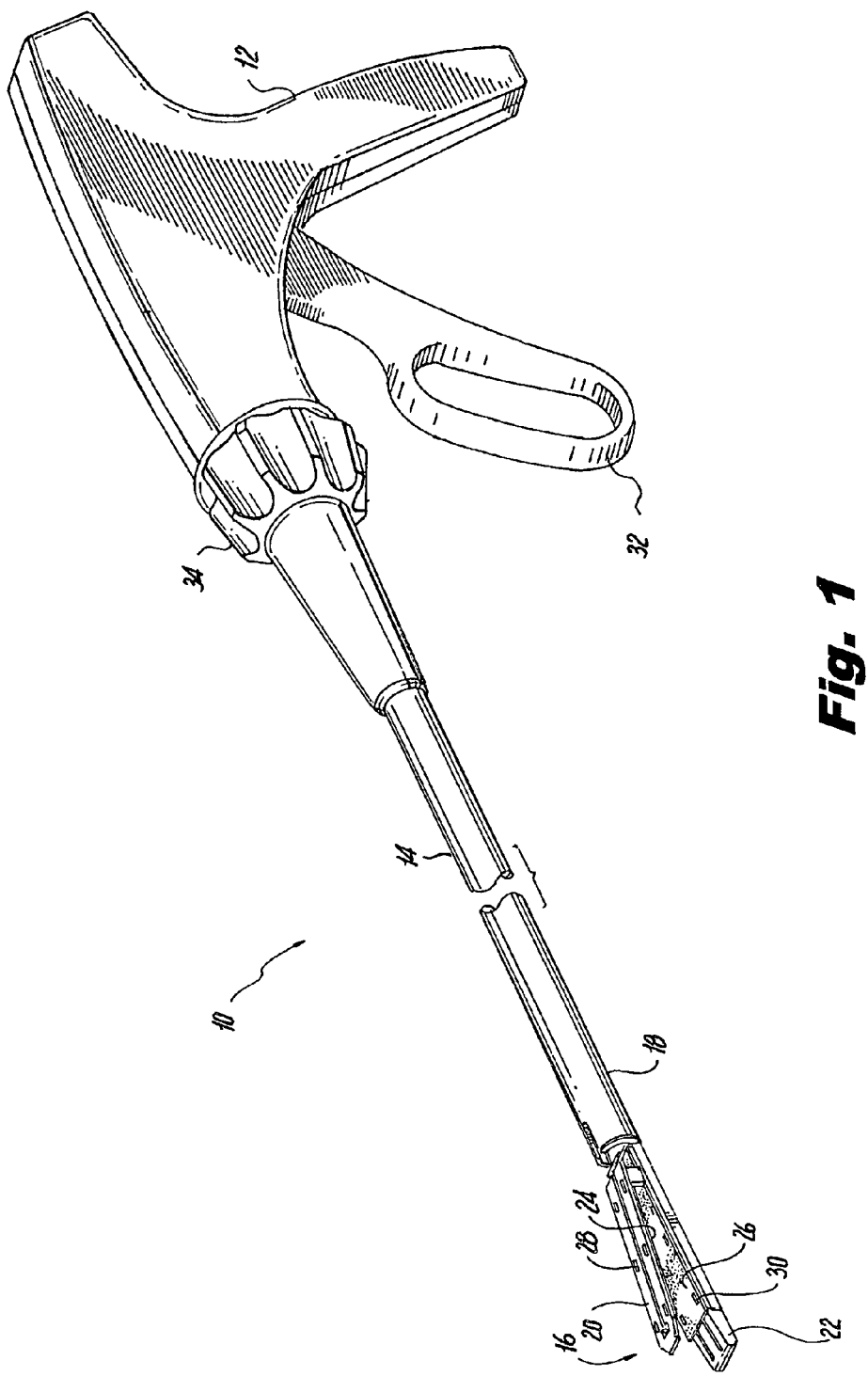
FIG. 1 is a perspective view of a surgical stapling instrument incorporating embodiments of retention systems for attachment of staple line buttress materials to an anvil and a staple cartridge.

Referring now to FIG. 1, there is disclosed a linear surgical stapling instrument or surgical stapler 10 for use in stapling tissue and applying layers of buttress material between the staples and underlying tissue. An exemplary example of this type of surgical stapling instrument is disclosed in U.S. Pat. No. 7,128,253, the entire disclosure of which is incorporated by reference herein. Surgical stapler 10 generally includes a handle 12 having an elongate tubular member 14 extending distally from handle 12. A jaw assembly 16 is mounted on a distal end 18 of elongate tubular member 14. Jaw assembly 16 includes a staple clinching anvil 20 and a staple containing cartridge or staple cartridge 22. Staple cartridge 22 may be permanently affixed to elongate tubular member 14 or may be detachable and thus replaceable with a new staple cartridge 22. Staple clinching anvil 20 is movably mounted on distal end 18 of elongate tubular member 14 and is movable between an open position spaced apart from staple cartridge 22 to a closed position substantially adjacent staple cartridge 22.

Staple clinching anvil 20 is provided with a layer of anvil buttress material 24 and staple cartridge 22 is provided with a layer of cartridge buttress material 26 in the manners described in more detail hereinbelow. A plurality of anvil buttress retainers in the form of clips or reverse staples 28 are provide to releasably secure anvil buttress material to staple clinching anvil 20. Likewise, a plurality of cartridge buttress retainers in the form of detachable clips or reverse staples 30 are provided to releasable secure cartridge buttress material 26 to staple cartridge 22. Anvil buttress material 24 and cartridge buttress material 26 are provided to reinforce and seal staple lines applied to tissue by surgical stapler 10.

Surgical stapler 10 includes a trigger 32 movably mounted on handle 12. Actuation of trigger 32 initially operates to move anvil 20 from the open to the closed position relative to staple cartridge 22 and subsequently actuate surgical stapler 10 to apply lines of staples to tissue. In order to properly orient jaw assembly 16 relative to the tissue to be stapled, surgical stapler 10 is additionally provided with a rotation knob 34 mounted on handle 12. Rotation of rotation knob 34 relative to handle 12 rotates elongate tubular member 14 and jaw assembly 16 relative to handle 12 so as to properly orient jaw assembly 16 relative to the tissue to be stapled.

Figure 2:
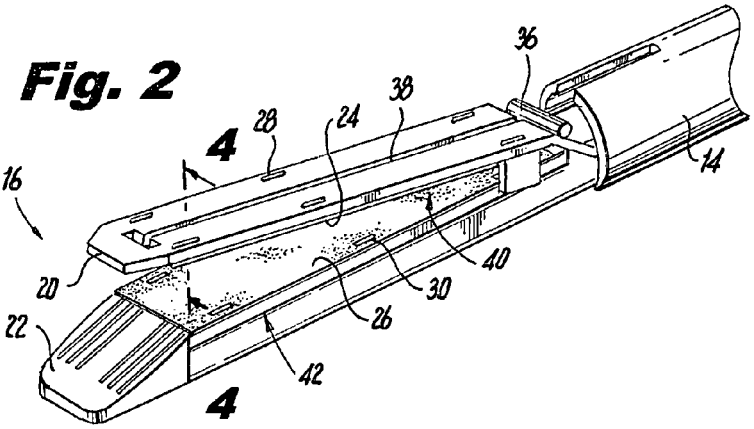
FIG. 2 is an enlarged perspective view of the distal end of the surgical stapling instrument of FIG. 1.

Referring to FIG. 2, a driver 36 is provided to move anvil 20 between the open and closed positions relative to staple cartridge 22. Driver 36 moves between a longitudinal slot 38 formed in anvil 20. A knife blade (not shown) is associated with driver 32 to cut tissue captured between anvil 20 and staple cartridge 22 as driver 36 passes through slot 38.

Anvil 20, anvil buttress material 24 and anvil buttress retainers or reverse staples 28 combine to form an anvil buttress attachment system 40 allowing anvil buttress material 24 to be supported on and releasably affixed to anvil 20. Similarly, staple cartridge 22, cartridge buttress material 26 and cartridge buttress retainers or reverse staples 30 combine to form a cartridge buttress attachment system 42 allowing cartridge buttress material 26 to be supported on and releasably affixed to staple cartridge 22. Anvil buttress attachment system 40 and cartridge buttress attachment system 42 are particularly configured to allow the respective buttress materials to be localized on inwardly facing surfaces of anvil 20 and staple cartridge 22 in order to facilitate passage of surgical stapler 10 into the body of a patient without risk of tearing or wrinkling of the respective buttress materials as surgical stapler 10 is inserted into and manipulated within the body of a patient.

Figure 3:
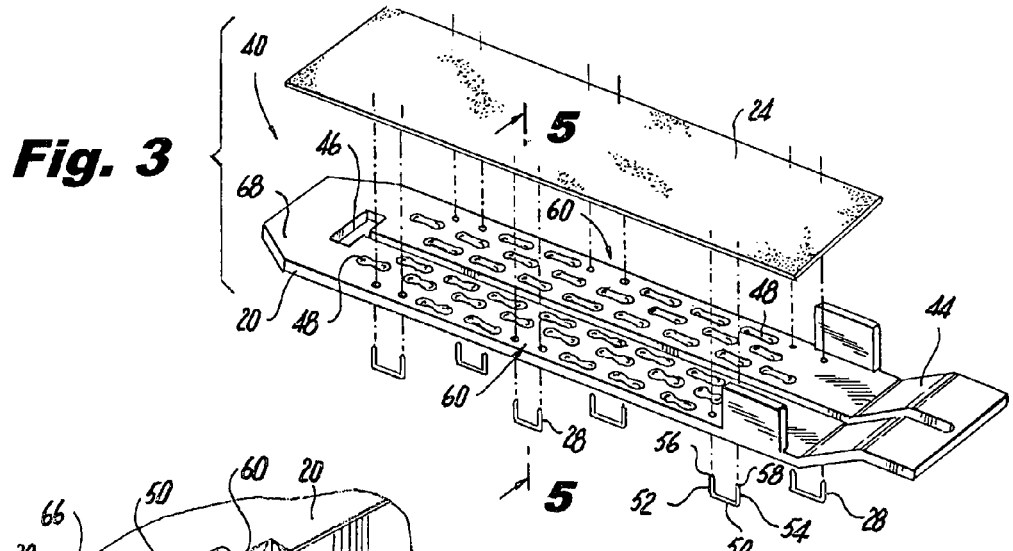
FIG. 3 is a perspective view, with parts separated, of one embodiment of an anvil and buttress material retention system.

Referring to FIG. 3, in order to move anvil 20 between the open and closed positions, anvil 20 includes a proximal, angled or sloped edge 44 configured to be engaged by driver 36 in order to cam anvil 20 to the closed position. Slot 38 extends distally from sloped edge 44 and terminates in a transverse slot 46 which is configured to capture driver 36 upon complete actuation of surgical stapler 10 to prevent any further actuation of surgical stapler 10. In order to secure staples provided by staple cartridge 22 about the tissues and buttress materials, anvil 20 is provided with longitudinally extending rows of staple clinching pockets 48 located on either side of longitudinal slot 38. While only a single row of staple clinching pockets 48 is illustrated on either side of slot 38, it is contemplated that multiple and/or staggered rows of staple clinching pockets 48 may be provided on anvil 20.

Referring still to FIG. 3, anvil buttress attachment system 40, including anvil 20, anvil buttress material 24 and anvil buttress retainers or reverse staples 28 will now be described. Anvil buttress material 24, as well as cartridge buttress material 26. The buttress material for the staple cartridge 22 and/or anvil 20 may be made from any biocompatible natural or synthetic material. The material from which the buttress material is formed may be bioabsorbable or non-bioabsorbable. It should of course be understood that any combination of natural, synthetic, bioabsorbable and non-bioabsorbable materials may be used to form the buttress material.

Some non-limiting examples of materials from which the buttress material may be made include but are not limited to poly(lactic acid), poly (glycolic acid), poly (hydroxybutyrate), poly (phosphazine), polyesters, polyethylene glycols, polyethylene oxides, polyacrylamides, polyhydroxyethylmethylacrylate, polyvinylpyrrolidone, polyvinyl alcohols, polyacrylic acid, polyacetate, polycaprolactone, polypropylene, aliphatic polyesters, glycerols, poly(amino acids), copoly (ether-esters), polyalkylene oxalates, polyamides, poly (iminocarbonates), polyalkylene oxalates, polyoxaesters, polyorthoesters, polyphosphazenes and copolymers, block copolymers, homopolymers, blends and combinations thereof.

In embodiments, natural biological polymers are used in forming the buttress material. Suitable natural biological polymers include, but are not limited to, collagen, gelatin, fibrin, fibrinogen, elastin, keratin, albumin, hydroxyethyl cellulose, cellulose, hydroxypropyl cellulose, carboxyethyl cellulose, chitan, chitosan, and combinations thereof. In addition, the natural biological polymers may be combined with any of the other polymeric materials described herein to produce the buttress material.

The buttress material may be porous or non-porous, or combinations of porous and non-porous layers. Where the buttress material is non-porous, buttress material may retard or prevent tissue ingrowth from surrounding tissues thereby acting as an adhesion barrier and preventing the formation of unwanted scar tissue. Thus, in embodiments, the buttress material possesses anti-adhesion properties. Techniques for forming non-porous layers from such materials are within the purview of those skilled in the art and include, for example, casting, molding and the like.

In embodiments, the buttress material is porous and possesses hemostatic properties. Where the buttress material is porous, it has openings or pores over at least a portion of a surface thereof. Suitable materials for forming the porous layer include, but are not limited to foams (e.g., open or closed cell foams). In embodiments, the pores may be in sufficient number and size so as to interconnect across the entire thickness of the porous layer. In other embodiments, the pores do not interconnect across the entire thickness of the porous layer. In yet other embodiments, the pores do not extend across the entire thickness of the porous layer, but rather are present at a portion of the surface thereof. In embodiments, the openings or pores are located on a portion of the surface of the porous layer, with other portions of the porous layer having a non-porous texture. Those skilled in the art reading the present disclosure will envision other pore distribution patterns and configurations for the porous layer.

Where the buttress material is porous, the pores may be formed using any method suitable to forming a foam or sponge including, but not limited to the lyophilization or freeze-drying of a composition. Suitable techniques for making foams are within the purview of those skilled in the art. Porous buttress materials can be at least 0.2 cm thick, in embodiments from about 0.3 to about 1.5 cm thick. Porous buttress materials can have a density of not more than about 75 mg/cm$^2$ and, in embodiments below about 20 mg/cm$^2$. The size of the pores in the porous buttress materials can be from about 20 μm to about 300 μm, in embodiments from about 100 μm to about 200 μm.

The buttress material may also include a reinforcement member. The reinforcement member may be associated with a porous or non-porous layer or may be positioned between a non-porous layer and a porous layer of the buttress material. Alternatively, the reinforcement member may be positioned entirely within one or more of the individual layers (i.e., embedded within the porous layer, the non-porous layer, or both) of the buttress material. It is also envisioned that the reinforcement member may be positioned at the surface of one of the layers making up the buttress material and, in embodiments, may be positioned at an exterior surface of the buttress material.

Some suitable non-limiting examples of reinforcement members include fabrics, meshes, monofilaments, multifilament braids, chopped fibers (sometimes referred to in the art as staple fibers) and combinations thereof. Where the reinforcement member is a mesh, it may be prepared using any technique known to those skilled in the art, such as knitting, weaving, tatting, knipling or the like. Where monofilaments or multifilament braids are used as the reinforcement member, the monofilaments or multifilament braids may be oriented in any desired manner. For example, the monofilaments or multifilament braids may be randomly positioned with respect to each other within the buttress material. As another example, the monofilaments or multifilament braids may be oriented in a common direction within the buttress material. Where chopped fibers are used as the reinforcement member, the chopped fibers may be oriented in any desired manner. For example, the chopped fibers may be randomly oriented or may be oriented in a common direction. The chopped fibers can thus form a non-woven material, such as a mat or a felt. The chopped fibers may be joined together (e.g., by heat fusing) or they may be unattached to each other. The chopped fibers may be of any suitable length. For example, the chopped may be from 0.1 mm to 100 mm in length, in embodiments, 0.4 mm to 50 mm in length. In an illustrative embodiment, the buttress material has randomly oriented chopped fibers that have not been previously fused together embedded within in the buttress material.

It is envisioned that the reinforcement member may be formed from any bioabsorbable, non-bioabsorbable, natural, or synthetic material previously described herein and combinations thereof. Where monofilaments or multifilament braids are used as the reinforcement member, any commercially available suture material may advantageously be employed as the reinforcement member.

In embodiments, at least one bioactive agent may be combined with the buttress material and/or any of the individual components (the porous layer, the non-porous layer and/or the reinforcement member) used to construct the buttress material. In these embodiments, the buttress material can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of bioactive agents may be used.

Anti-adhesive or anti-adhesion agents can be used to prevent adhesions from forming between the buttress material and the surrounding tissues opposite the target tissue. Some examples of these agents include, but are not limited to poly (vinyl pyrrolidone), carboxymethyl cellulose, hyaluronic acid, polyethylene oxide, poly vinyl alcohols and combinations thereof.

Suitable antimicrobial agents which may be included as a bioactive agent in the buttress material of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in the buttress material in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; antiparkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable bioactive agents which may be included in the coating composition include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); protein inhibitors, protein antagonists, and protein agonists; nucleic acids, such as antisense molecules, DNA and RNA; oligonucleotides; polynucleotides; and ribozymes.

Figure 4:
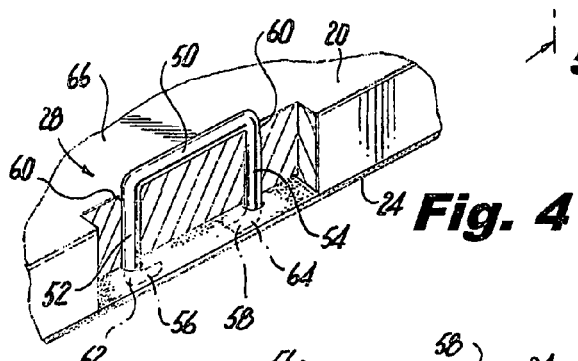
FIG. 4 is a perspective view, partially shown in section, taken along line 4-4 of FIG. 2.
Figures 5, 6:
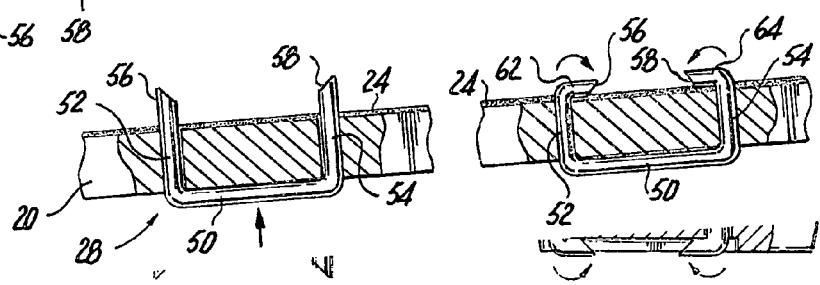
FIG. 5 is a side view, partially shown in section, taken along line 5-5 of FIG. 3 illustrating initial assembly of an anvil buttress retention system.
FIG. 6 is a side view, partially shown in section, illustrating the partial crimping of a retaining clip of the anvil buttress retention system.

Referring now to FIGS. 3-6, and initially with regard to FIGS. 3 and 5, the details of anvil buttress retention system 40 will now be described. As noted above, anvil buttress retention system 40 includes clip or reverse staple 28 to secure anvil buttress material 24 to anvil 20. Reverse staple 28 has a span or back span 50 having a pair of legs 52 and 54 extending from backspan 50. Legs 52 and 54 terminate in sharp tips 56 and 58, respectively, which are provided to penetrate anvil buttress material 24 as anvil retention system 40 is assembled.

As noted above, anvil 20 is provided with rows of staple clinching pockets 48. In this embodiment, pairs of holes 60 are drilled in anvil 20 to allow legs 52 and 54 of reverse staples 28 to pass therethrough. Pairs of holes 60 are positioned in line with rows of staple clinching pockets 48 and take the place of one or more sets of staple clinching pockets 48 within the rows as shown. In a specific embodiment, pairs of holes 60 are located in the outer most rows of staple clinching pockets 48 to secure anvil buttress material 24 along its outer edges.

Referring now to FIGS. 3-6, in order to assemble anvil buttress retention system 40, legs 52 and 54 of reverse staples 28 are inserted through pairs of holes 60 in anvil 20 such tips 56 and 58 penetrate anvil buttress material 24 (FIG. 5). Alternatively, anvil buttress material 24 may be provided with preformed holes to accommodate legs 52 and 54. Once legs 52 and 54 have been positioned through anvil 20 and anvil buttress material 24, legs 52 and 54 are bent or crimped to form inwardly bent legs 62 and 64 (see FIG. 6) which secure anvil buttress material 24 against anvil 20. As shown, backspan 50 of reverse staple 28 is adjacent a top side 66 of anvil 20 while anvil buttress material 24 is secured against an underside 68 of anvil 20 by inwardly bent legs 62 and 64 (FIGS. 4 and 6). The length of inwardly bent legs 62 and 64 is sufficiently short such that anvil buttress material 24 can pull away from anvil 20 once anvil buttress material 24 has been stapled to tissue.

Referring now to FIGS. 7-10, the details and assembly of cartridge buttress retention system 42 will now be described. Referring initially to FIG. 7, and as noted above, cartridge buttress retention system 42 generally includes staple cartridge 22, cartridge buttress material 26 and detachable clips or reverse staples 30 releasably securing cartridge buttress material 26 to staple cartridge 22. Reverse staples 30 are similar to the staples, described below, used to staple tissue. In contrast to reverse staples 28 associated with anvil buttress retention system 40 described above, reverse staples 30 are intended to detach from staple cartridge 22 and travel with cartridge buttress material 26 as cartridge buttress material 26 is stapled to a body. Reverse staples 30 are formed of a biocompatible material and may be formed from an absorbable or resorbable material so as to deteriorate within the body over time. In contrast to reverse staples 28 associated with anvil buttress retention system 40 described above, reverse staples 30 are intended to detach from staple cartridge 22 and travel with cartridge buttress material 26 as cartridge buttress material 26 is stapled to a body.

Staple cartridge 22 generally includes a plastic body portion 70 and an outer channel 72. Staple cartridge 22 is supported on elongate tubular member 14 by outer channel 72. Body portion 70 includes a plurality of rows of staple containing pockets 74 provided to contain staples used to staple tissue as described below. A knife channel 78 is positioned between rows of staple containing pockets 74 for passage of a knife used to cut the stapled tissue along with cartridge buttress material 26.

Rows of staple containing pockets 74 include longitudinally spaced, empty or dummy pockets 78 for receipt of reverse staples 30 in order to secure cartridge buttress material 26 to staple cartridge 22.

As shown in FIG. 8, in order to assemble cartridge buttress retention system 42, cartridge buttress material 26 is positioned over body portion 70 of staple cartridge 22 and reverse staples 30 are inserted through cartridge buttress material 26 and into dummy pockets 78 (FIG. 9). With reference to FIGS. 9 and 10, a crimping die 80 is provided to frictionally secure reverse staple 30 within dummy pocket 78. Specifically, reverse staple 30 includes a back span 82 and a pair of legs 84 and 86 projecting from back span 82. Legs 84 and 86 terminate in points or tips 88 and 90, respectively.

Referring to FIGS. 9 and 10, once legs 84 and 86 have been inserted through cartridge buttress material 26 and into dummy pocket 78, crimping die 80 is urged upwardly within dummy pocket 78 such that crimping pockets 92 and 94 on crimping die 80 engage tips 88 and 90 and bend or crimp them to form crimped ends 96 and 98 (FIG. 10). When reverse staple 30 has been crimped within dummy pocket 78, legs 84 and 86 are forced or splayed outwardly so as to frictionally engage walls 100 of dummy pocket 78 thereby frictionally retaining reverse staple 30 within dummy pocket 78.

Figure 11:
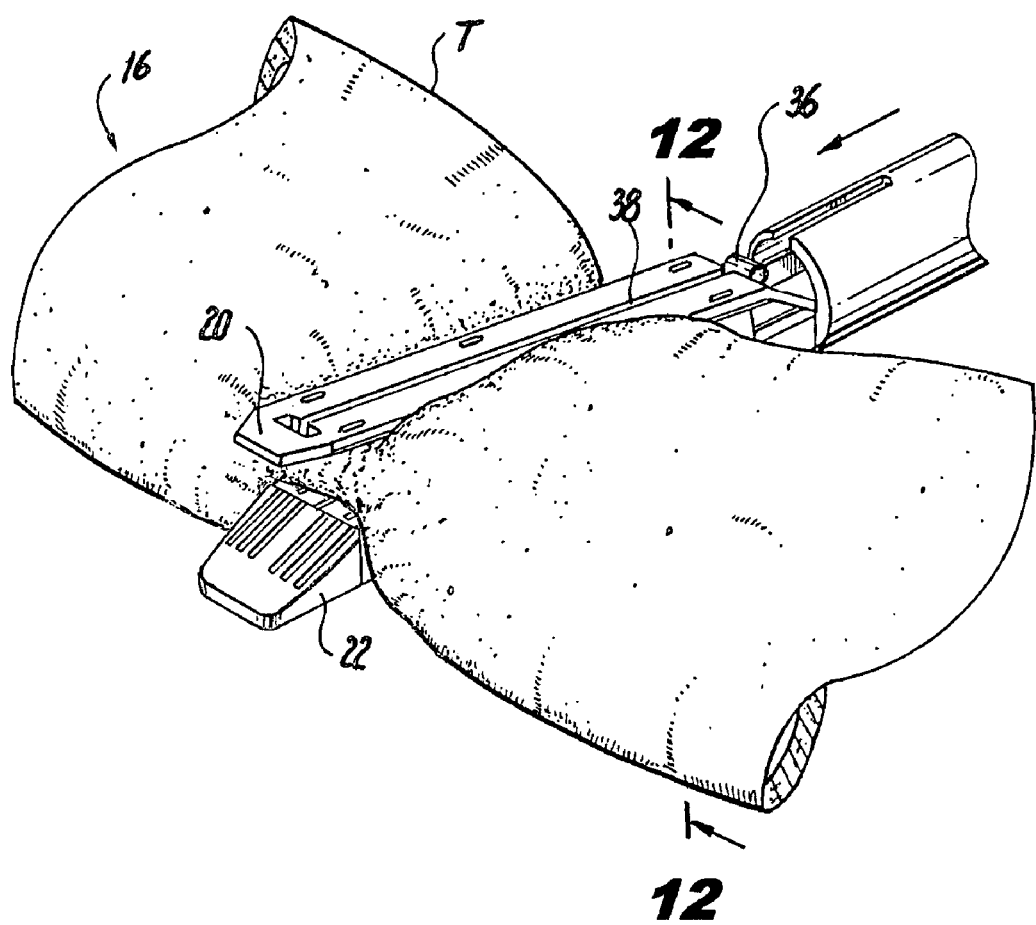
FIG. 11 is a perspective view of the distal end of the surgical stapling instrument of FIG. 1 positioned about a tissue section.
Figure 12:
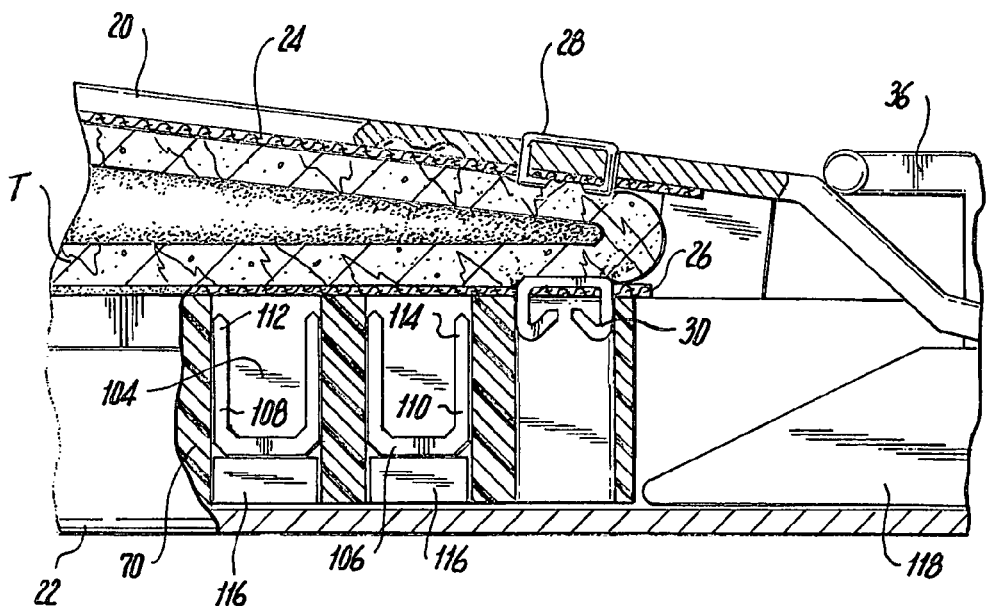
FIG. 12 is a cross-sectional view of the tissue section positioned between the anvil assembly and the cartridge assembly of the surgical stapling instrument of FIG. 1.

Referring now to FIGS. 11 through 17, and initially with respect to FIGS. 11 and 12, the use of surgical stapler 10 to staple and divide a tubular tissue section T will now be described. Initially, jaw assembly 16, including anvil 20 and staple containing cartridge 22 are positioned around the tissue T to be stapled. Driver 36 is in a proximal position relative to anvil slot 38. As best shown in FIG. 11, the staple containing insert or plastic body portion 70 includes staples 102 positioned within individual staple pockets 104 of row of staple pockets 74. Staples 102 are of a conventional type and include a backspan 106 having a pair of legs 108 and 110 extending from backspan 106. Legs 108 and 110 terminate in tissue penetrating tips 112 and 114. Pushers 116 are located within staple pockets 104 and are positioned between staples 102 and the path of a drive bar 118.

Figure 13:
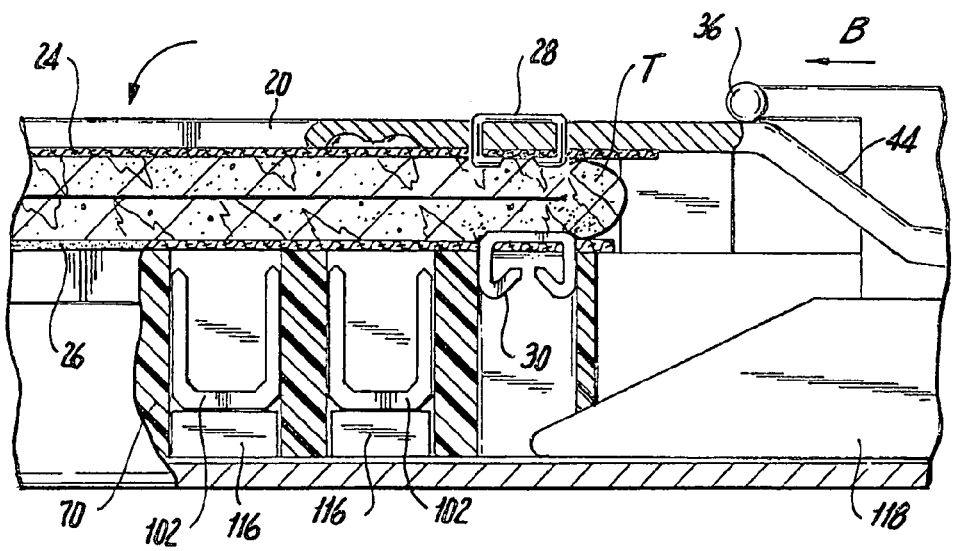
FIG. 13 is a cross-sectional view, similar to FIG. 12, during initial actuation of the surgical stapling instrument of FIG. 1.
Figure 14:
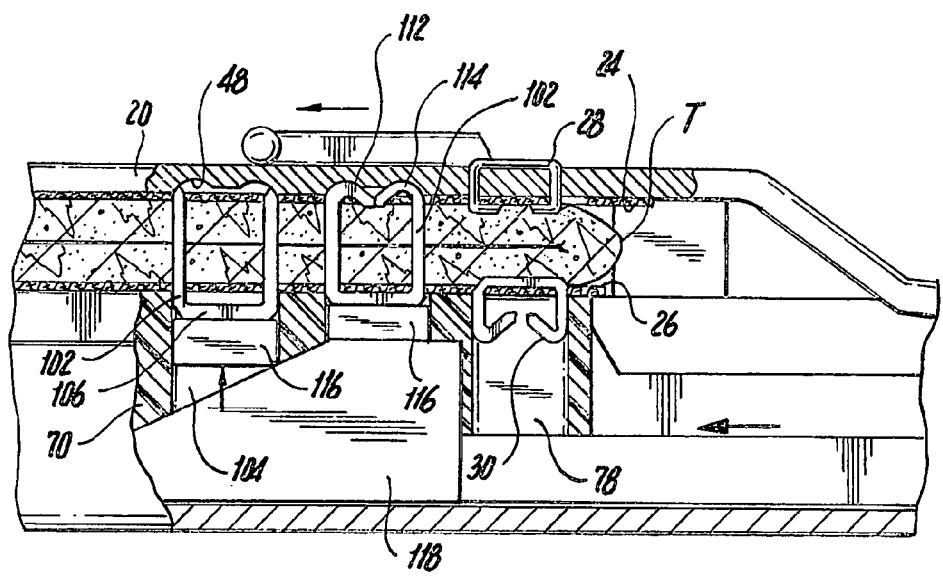
FIG. 14 is a cross-sectional view, similar to FIG. 13, during actuation of the surgical stapling instrument to staple the tissue section.

Referring now to FIG. 13, surgical stapler 10 is initially actuated by movement of trigger 32 relative to handle 12 (FIG. 1) causing driver 36 to move in the direction of arrow B and against sloped edge 44 of anvil 20 thereby causing anvil 20 to be moved to the closed position relative to staple cartridge 22. As best shown in FIG. 14, as drive bar 118 advances distally within plastic body portion 74, drive bar 118 urges pushers 116 upwardly against backspans 106 of staples 102 driving staples 102 through cartridge buttress material 26, tissue T, anvil buttress material 24 and towards staple clinching pockets 48 in anvil 20. Tissue penetrating tips 112 and 114 are bent within staple clinching pockets 48 in anvil 20 to thereby secure anvil buttress material 24 against tissue T while backspan 106 secures cartridge buttress material 26 against tissue T.

While not specifically shown, upon full actuation of surgical stapler 10, a knife blade associated with surgical stapler 10 and carried by driver 36 cuts tissue T, as well as anvil buttress material 24 and cartridge buttress material 26 between the rows of now clinched staples 102.

Figure 15:
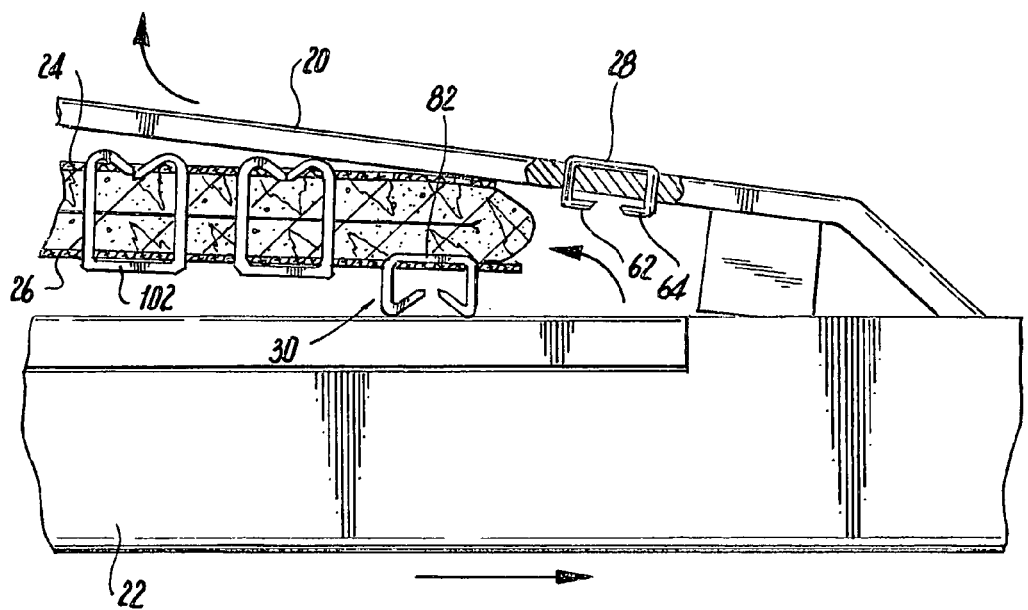
FIG. 15 is a cross-sectional view, similar to FIG. 14, after actuation illustrating release of the stapled tissue section.

As shown in FIG. 15, in one embodiment, upon movement of anvil 20 to the open position spaced apart from staple cartridge 22, anvil buttress material 24 pulls away from anvil 20 and anvil buttress retainers 28. Specifically, anvil buttress material 24 pulls free from inwardly bent legs 62 and 64 of anvil buttress retainers 28 leaving anvil buttress retainers 28 attached to anvil 20. In addition, as anvil 20 is moved to the open position, cartridge buttress material 26 separates from staple containing cartridge 22. As noted above, cartridge buttress retainers 30 are frictionally retained within dummy pockets 78. As cartridge buttress material 26 pulls away from staple containing cartridge 22, cartridge buttress retainers 30 pull free from dummy pockets 78 and remain with the stapled tissue T and cartridge buttress material 26. As noted above, cartridge buttress retainers 30 may be formed of absorbable or resorbable materials which will degrade in the body over time.

Figure 16:
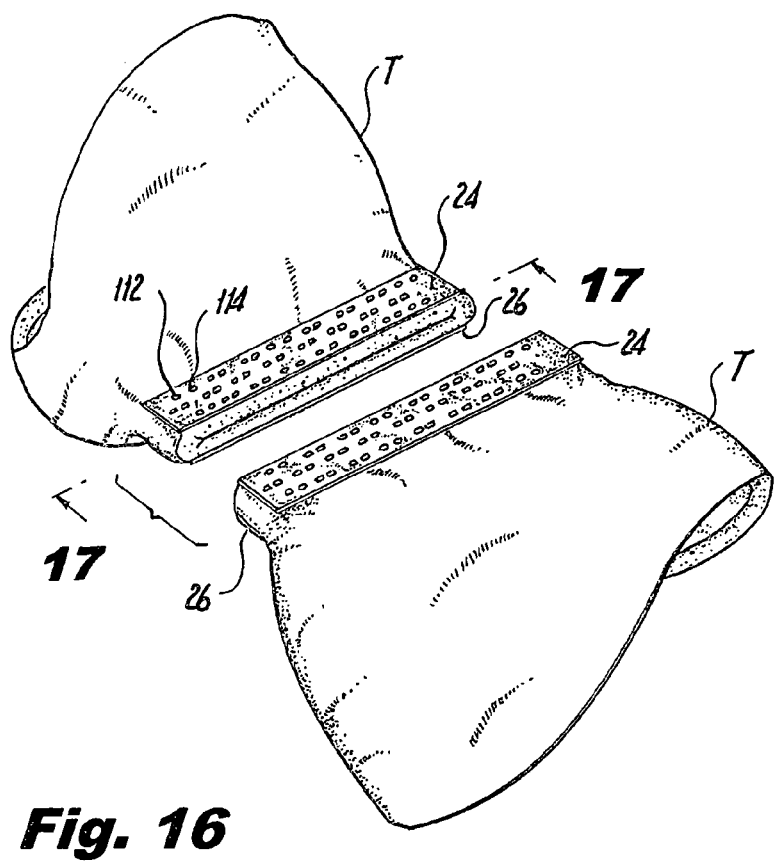
FIG. 16 is a perspective view of the stapled tissue section with buttress materials attached.
Figure 17:
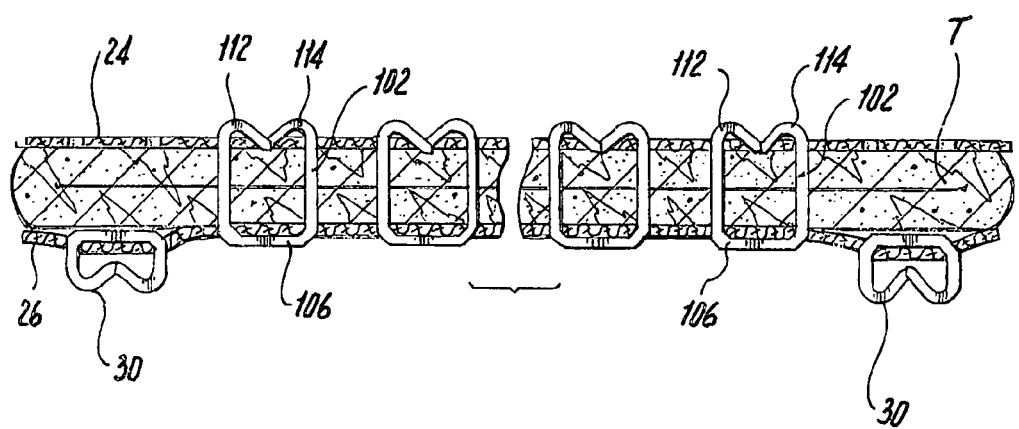
FIG. 17 is a cross-sectional view taken along line 17-17 of FIG. 16.

The resulting tissue T, divided and stapled closed with staples 102, is best illustrated in FIGS. 16 and 17. Specifically, cartridge buttress material 26 is secured against tissue T by backspans 106 of staples 102 and anvil buttress material 24 is secured against tissue T by the now clinched tissue penetrating tips 112 and 114 of staples 102. In this manner, anvil buttress material 24 and cartridge buttress material 26 are stapled to tissue T thereby sealing and reinforcing these staple lines created by staples 102.

Referring now to FIGS. 18-34, there are disclosed alternative embodiments of an anvil buttress retention system 120 and a cartridge buttress retention system 122 for use in surgical stapling instrument 10. Referring initially to FIGS. 18 and 19, anvil buttress retention system 120 is provided to retain anvil buttress material 24 against an anvil 124 prior to stapling to tissue. Anvil 124 is similar to anvil 20 described hereinabove and includes a sloped proximal edge 136 for engagement with driver 36 in order to move anvil 124 between open and closed positions relative to staple containing cartridge 22. Anvil 124 additionally includes a slot 128 for passage of a knife associated with surgical stapling instrument 10. Anvil buttress retention system 120 includes a plurality of novel retainers or clips 130 to assist in retaining anvil buttress material 24 on anvil 124. Anvil 124 is provided with a series of clip slots 132, for receipt of clips 130, which are spaced along staple clinching pockets 134 formed in anvil 124. Anvil buttress material 24 also contains buttress material slots 136 for passage of clips 130 therethrough.

Referring for the moment to FIG. 20, clip 130 is generally formed as a plate 138 having a sloped edge 140 along a first end 142 of plate 138 and a flange or lip 144 projecting at approximately a right angle from a second end 146 of plate 138. Sloped edge 140 is configured to be engaged by driver 36 to force clip 130 out of anvil 124 while lip 144 is provided to retain anvil buttress material 24 against anvil 124 prior to stapling. As best shown in FIGS. 20 and 21, clip 130 is frictionally retained within clip slot 132 of anvil 124 and an undersurface 148 of lip 144 retains anvil buttress material 24 against anvil 124.

In an alternative embodiment shown in FIG. 22, an alternative clip 150 may be provided having a pair of spaced apart lips 152 and 154 projecting at a generally right angle from a plate 156 of clip 150. Lips 152 and 154 are configured to retain anvil buttress material 24 against anvil 124 in a manner similar to that of clip 130. Clip 150 also includes an angled edge 158 for engagement by driver 36 of surgical stapling instrument 10 to separate clip 150 and anvil buttress material 24 from anvil 124.

A still further embodiment of a retention clip 160 is illustrated in FIG. 23. Clip 160 is also formed as a plate 162 having an angled edge 164 for engagement with driver 30 of surgical stapling instrument 10. Clip 160 is provided with a pair of opposite facing lips 166 and 168 which extend generally at right angles from plate 162 to increase the amount of surface provided to secure anvil buttress material 24 to anvil 124.

Figure 24:
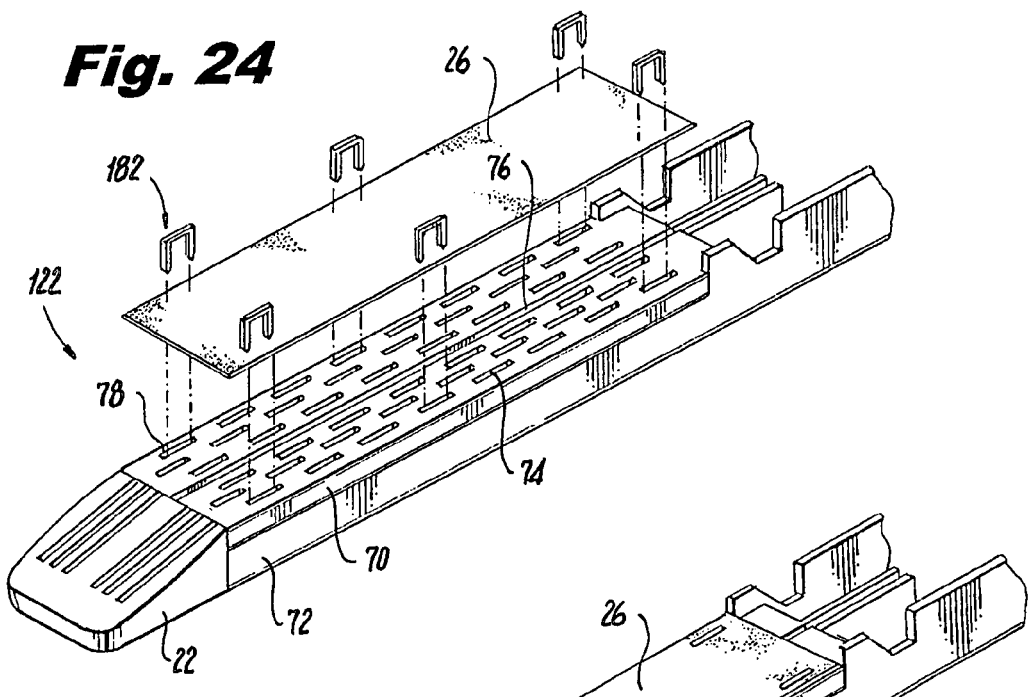
FIG. 24 is a perspective view, with parts separated, of another embodiment of a staple cartridge and buttress material retention system in accordance with FIG. 18.
Figure 25:
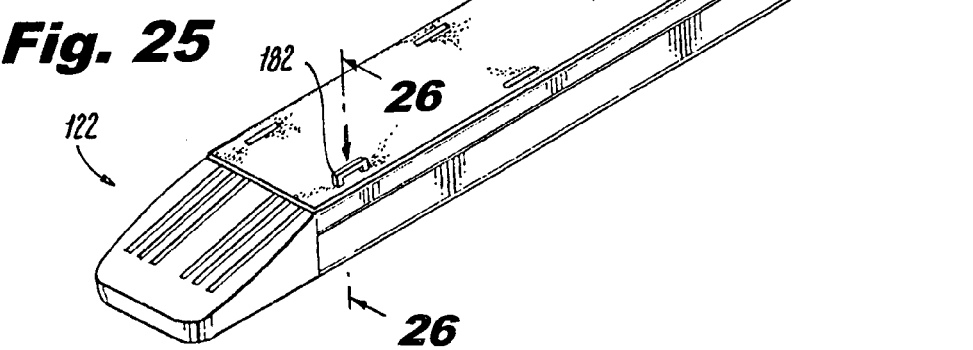
FIG. 25 is a perspective view of a staple illustrating the partially assembled staple cartridge buttress retention system of FIG. 24.
Figure 26:
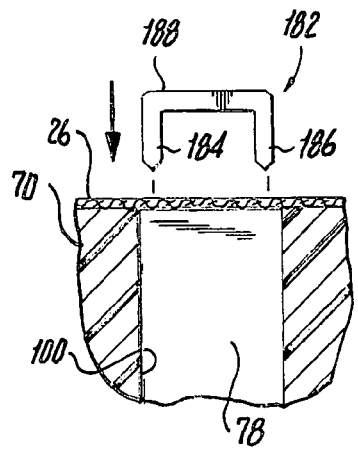
FIG. 26 is a side view, partially shown in section, illustrating the insertion of a reverse staple being inserted into a staple pocket.
Figure 27:
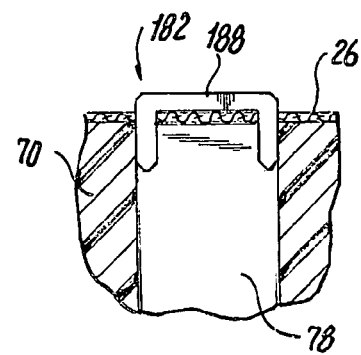
FIG. 27 is a side view, partially shown in section, illustrating the reverse staple frictionally retained in the staple pocket.

Referring now to FIGS. 22-27, and initially with regard to FIG. 24, cartridge buttress retention system 122 is similar to cartridge buttress retention system 42 described hereinabove, including staple containing cartridge 22 having plastic body portion 70 and outer channel 72 and cartridge buttress material 26. As described hereinabove, plastic body portion includes rows of staple pockets 74 separated by knife channel 76. However, in place of reverse staples 30, cartridge buttress retention system 122 utilizes clips or reverse staples 182 which are not intended to be crimped within dummy pockets 78 in plastic body portion 70. Rather, as best shown in FIGS. 26 and 27, legs 184 and 186 of reverse staple 182 frictionally engage inner surfaces 100 of dummy pockets 78 while a back span 188 of reverse staple 182 holds cartridge buttress material 26 against staple containing cartridge 22.

Figure 28:
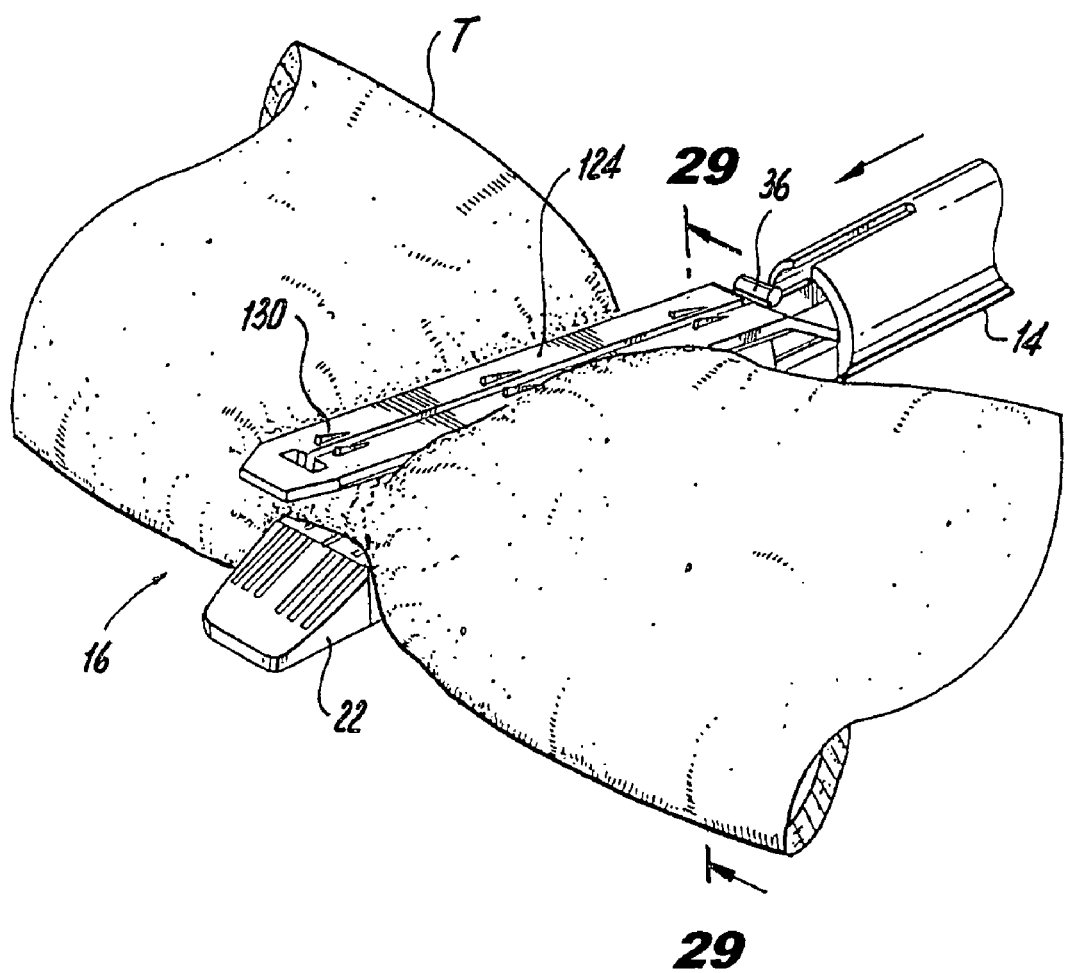
FIG. 28 is a perspective view of the distal end of the surgical stapling instrument illustrated in FIG. 18 positioned about a tissue section.
Figure 29:
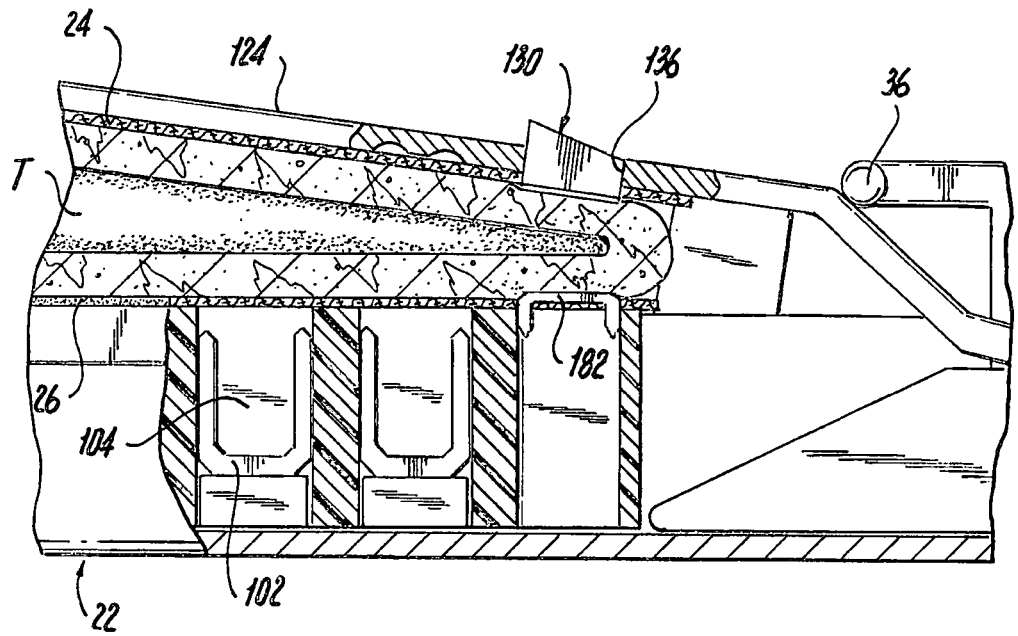
FIG. 29 is a cross-sectional view taken along the line 29-29 of FIG. 28.

With reference to FIGS. 28 and 29, in use, jaw assembly 16 is initially positioned about a tissue section T with anvil 124 in the open position space apart from staple containing cartridge 22. Driver 36 is in a proximal position relative to sloped proximal edge 126 of anvil 24. Clips 130 are positioned through slots 136 in anvil 124 retaining anvil buttress material 24 against anvil 124. As discussed hereinabove, plastic body portion 70 contains staples 102 positioned within staple pockets 104. Reverse staples 182 are positioned within dummy pockets 78 retaining staple buttress material 26 against staple containing cartridge 22.

Figure 30:
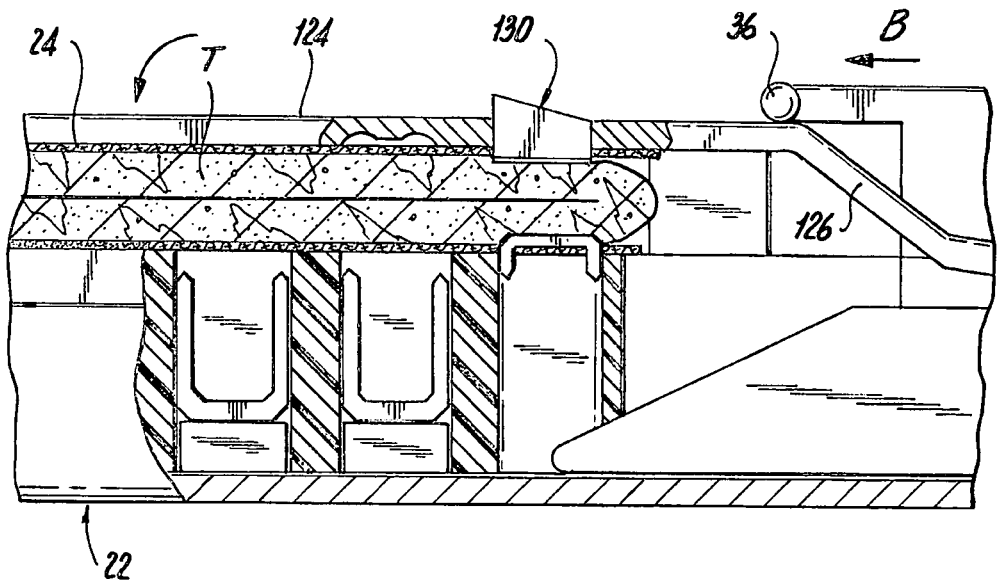
FIG. 30 is a cross-sectional view, similar to FIG. 29, during initial actuation.

Referring now to FIG. 30, upon actuation of surgical stapler 10, driver 36 moves distally in the direction of arrow B and against sloped edge 126 of anvil 124 causing anvil 124 to move to the closed position relative to staple containing cartridge 22 compressing tissue T therebetween.

Figure 31:
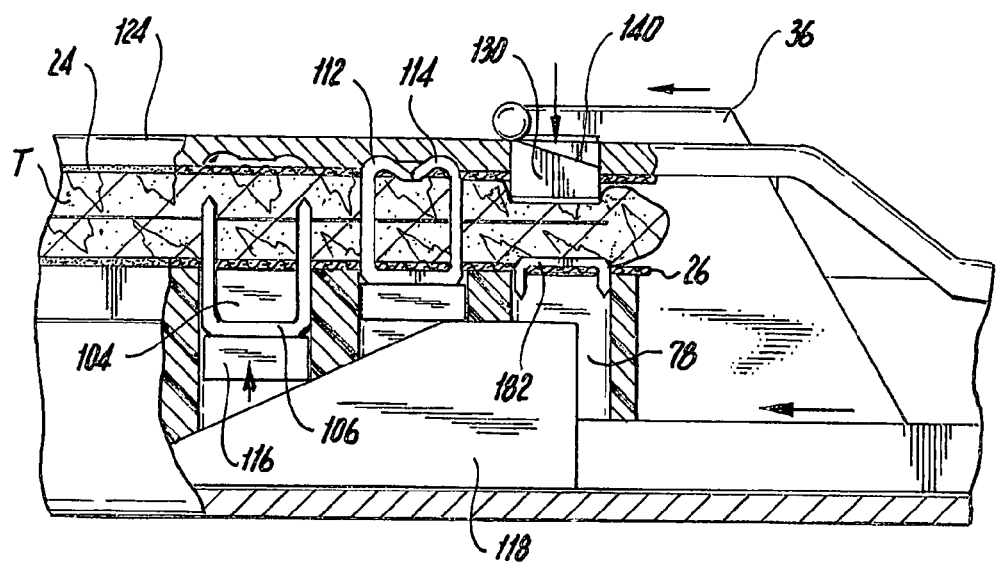
FIG. 31 is a cross-sectional view, similar to FIG. 30, during actuation to staple the tissue section.

As best shown in FIG. 31, as driver 36 continues to move distally along anvil 124, driver 36 engages sloped edge 140 of clips 130 forcing clips 130 downwardly within slots 132 in anvil 124. This initiates release of anvil buttress material 24 from anvil 124. Identical to that described hereinabove, as drive bar 118 advances distally in response to actuation of surgical stapler 10, drive bar 118 urges pushers 116 upwardly within staple pockets 104 driving tissue penetrating tips 112 and 114 of staple 102 through cartridge buttress material 26, tissue T, anvil buttress material 24 and into staple clinching pockets 134 in anvil 124. Tips 112 and 114 are crimped within staple clinching pockets 124 thereby securing anvil buttress material 24 to tissue T. Backspans 106 of staples 102 secure cartridge buttress material 26 to tissue T. As discussed above, a knife associated with surgical stapler 10 divides tissue T, as well as anvil buttress material 24 and cartridge buttress material 26, between now clinched rows of staples 102.

Figure 32:
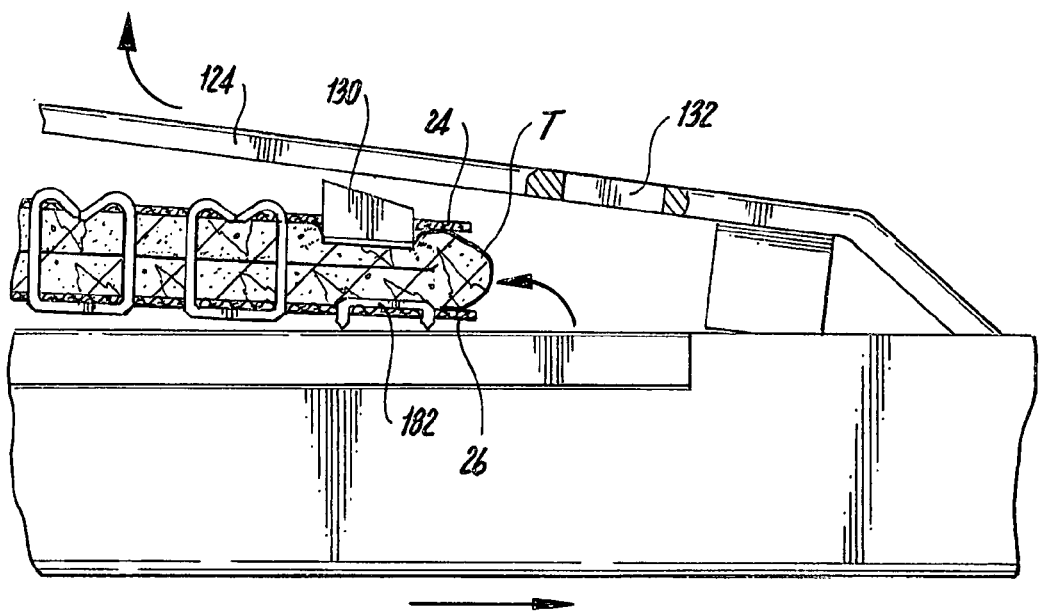
FIG. 32 is a cross-sectional view, similar to FIG. 31, after actuation illustration release of the stapled tissue section.

Referring for the moment to FIG. 32, upon movement of anvil 124 to the open position, anvil buttress material pulls clips 130 out of clip slots 132 in anvil 124 such that anvil buttress material 24 separates from anvil 124. Reverse staples 182 pull free from dummy pockets 78 (FIG. 31) freeing cartridge buttress material 26 from staple cartridge 22. Thus, both reverse staples 182 and clips 130 remain with stapled tissue T and, as noted above, are formed of a degradable material which will dissolve within the body over time.

Figure 33:
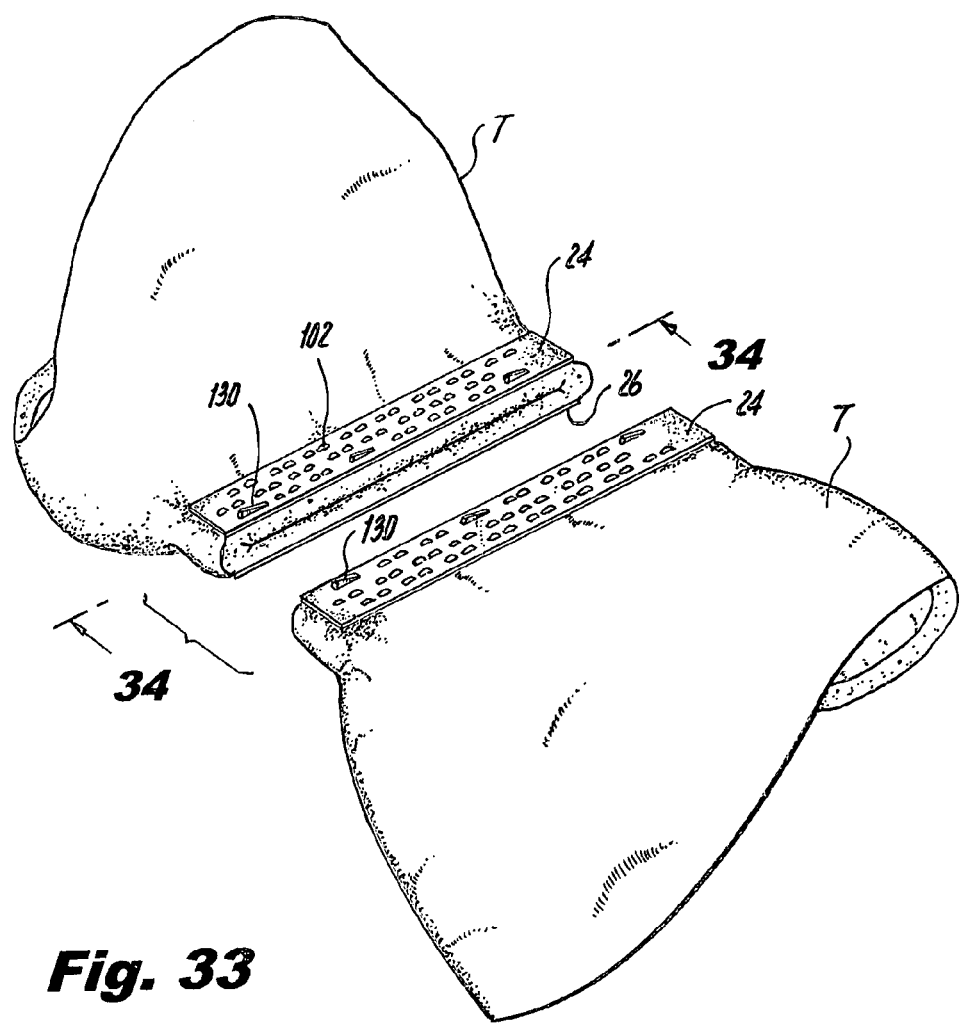
FIG. 33 is a perspective view of the stapled tissue section with buttress material attached.
Figure 34:
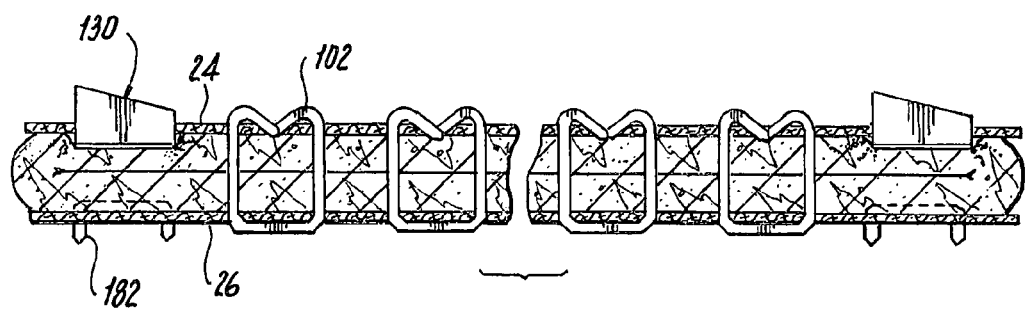
FIG. 34 is side view, partially shown in section, taken along line 34-34 of FIG. 33.

The resultant stapled tissue sections T are best illustrated in FIGS. 33 and 34. Cartridge buttress material 26 and anvil buttress material 24 are stapled to tissue T by staples 102 thereby reinforcing the staple line formed by staples 102 and sealing the stapled and severed ends of tissue T.

Referring now to FIGS. 35-44, there is disclosed a further alternative embodiment of a cartridge buttress retention system 190 for use with surgical stapler 10 and anvil buttress retention system 40 described hereinabove. Cartridge buttress retention system 190 generally includes staple containing cartridge 22 and cartridge buttress material 26. A plurality of cartridge buttress retainers or I-beam retainers 192 are provided to frictionally engage staple containing cartridge 22 and temporarily secure cartridge buttress material 26 to staple containing cartridge 22.

Figures 35, 36, 37, 38:
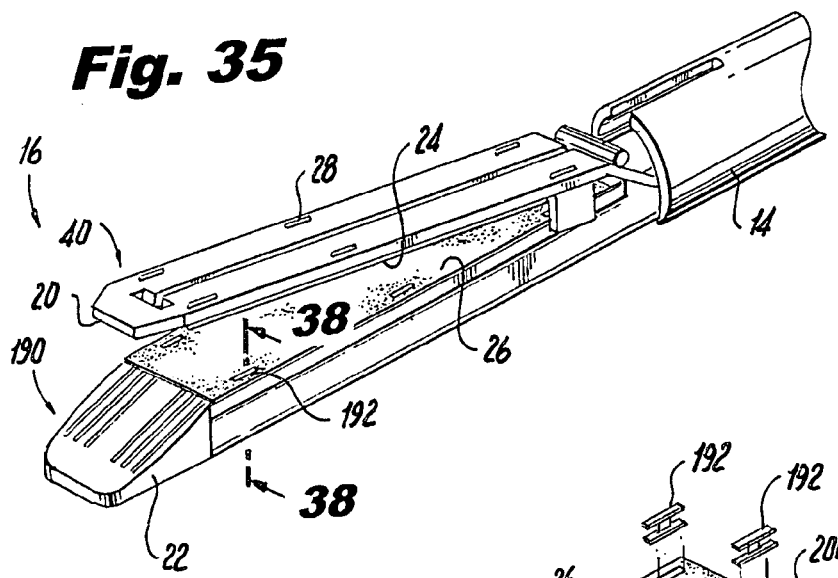
FIG. 35 is an enlarged perspective view of the distal end of the surgical stapling instrument of FIG. 1 incorporating further alternative embodiments of retention systems for attachment of staple line buttress materials to an anvil and staple cartridge.
FIG. 36 is a perspective view, with parts separated, of a staple cartridge buttress retention system in accordance with FIG. 35.
FIG. 37 is a perspective view of an I-beam retention clip of the staple cartridge buttress retention system of FIG. 36.
FIG. 38 is a side view, partially shown in section, of the I-beam retention clip frictionally retained within the staple cartridge.
Figure 39:
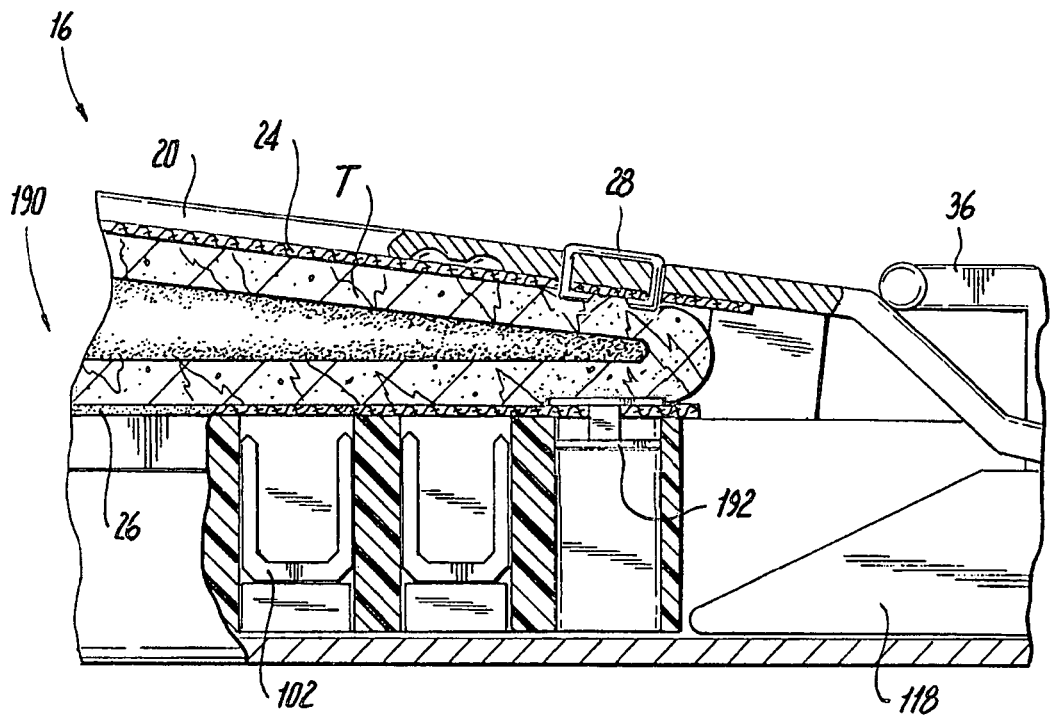
FIG. 39 is a cross-sectional view of a tissue section positioned between the anvil and cartridge assemblies of FIG. 35.

Referring for the moment to FIG. 37, I-beam retainer 192 generally includes a rectangular central portion 194 having rectangular upper beam 196 and lower beam 198 attached thereto. As with the retention devices described hereinabove, retainer 192 may be formed of a material that degrades within the body over time. Cartridge buttress material 26 includes a plurality of slots 200 which are aligned with dummy pockets 78 in staple containing cartridge 22 and allow for partial passage of I-beam retainer 192 therethrough (FIG. 36).

With continued reference to FIG. 37 and also FIG. 38, an under surface 102 of upper beam 196 of I-beam retainer 192 secures cartridge buttress material 26 against staple containing cartridge 22. Opposed ends 204 and 206 of lower beam 198 of I-beam retainer 192 frictionally engage inner surfaces 100 of dummy pockets 78 to frictionally retain I-beam retainer 192 partially within staple containing cartridge 22.

Figure 40:
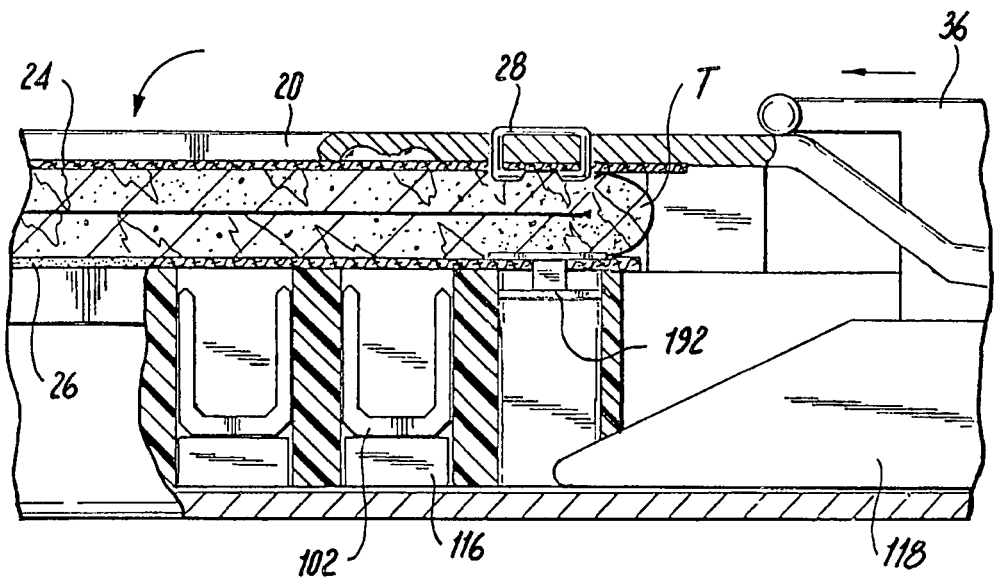
FIG. 40 is a cross-sectional view, similar to FIG. 39, during initial actuation.
Figure 41:
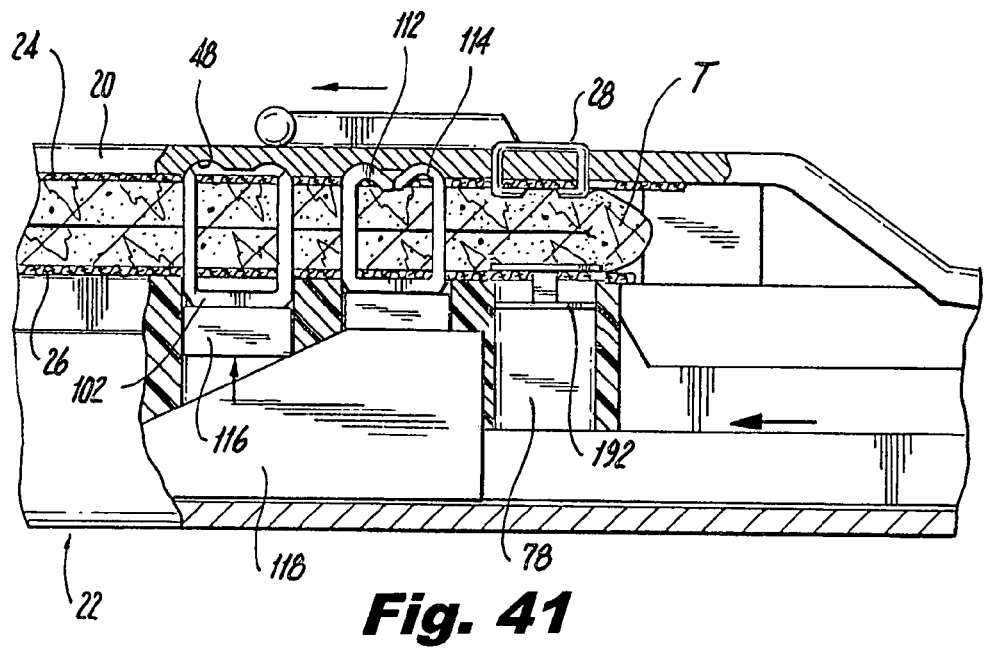
FIG. 41 is a cross-sectional view, similar to FIG. 40, during actuation to staple the tissue section.
Figure 42:
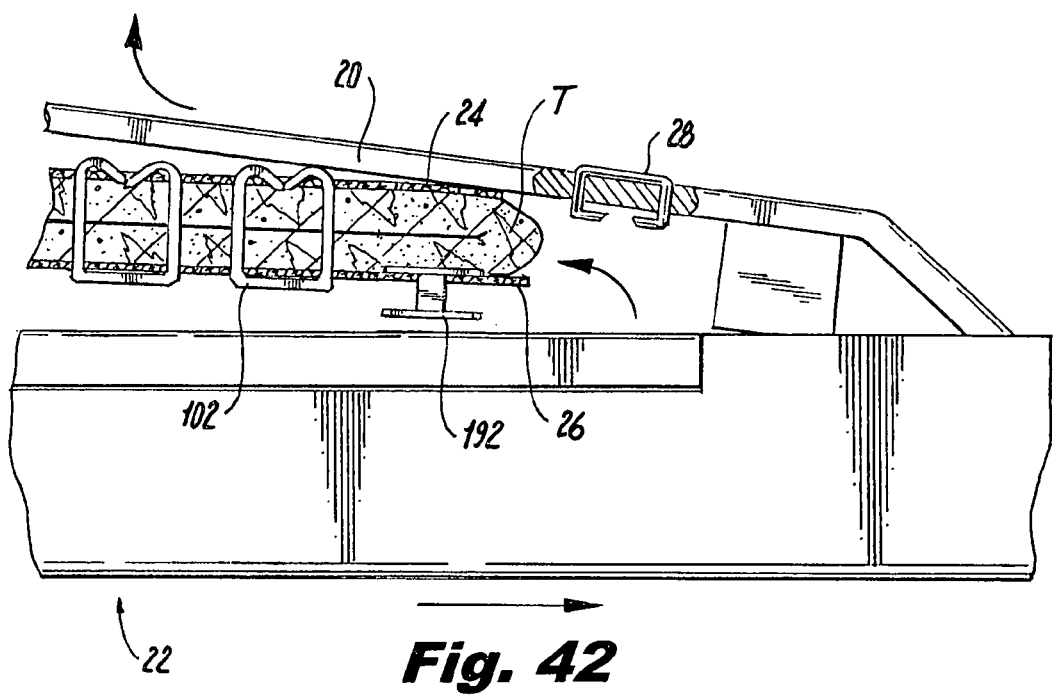
FIG. 42 is a cross-sectional view, similar to FIG. 41, after actuation illustrating release of the stapled tissue section.

With reference to FIGS. 39-42, operation of cartridge buttress retention system 190 functions similar to that of cartridge buttress retention systems 42 and 122 described herinabove. Initially, jaw assembly 16 is positioned about tissue T with anvil 20 is in the open position spaced apart from staple containing cartridge 22. Upon actuation of surgical stapler 10, driver 36 advances distally moving anvil 20 to the closed position (FIG. 40). Drive bar 118 advance distally engaging pushers 116 and driving staples 102 through cartridge buttress material 26, tissue T, anvil buttress material 24 and into staple clinching pockets 48 to clinch tips 112 and 114 of staples 102 over anvil buttress material 24 (FIG. 41). Upon movement of anvil 20 to the open position, anvil buttress material 24 pulls free from reverse staples 28. Lower beam 198 is sufficiently flexible to allow I-beam retainer 192 to pull free from dummy pocket 78 and remain affixed to cartridge buttress material 26 (FIG. 42).

Figure 43:
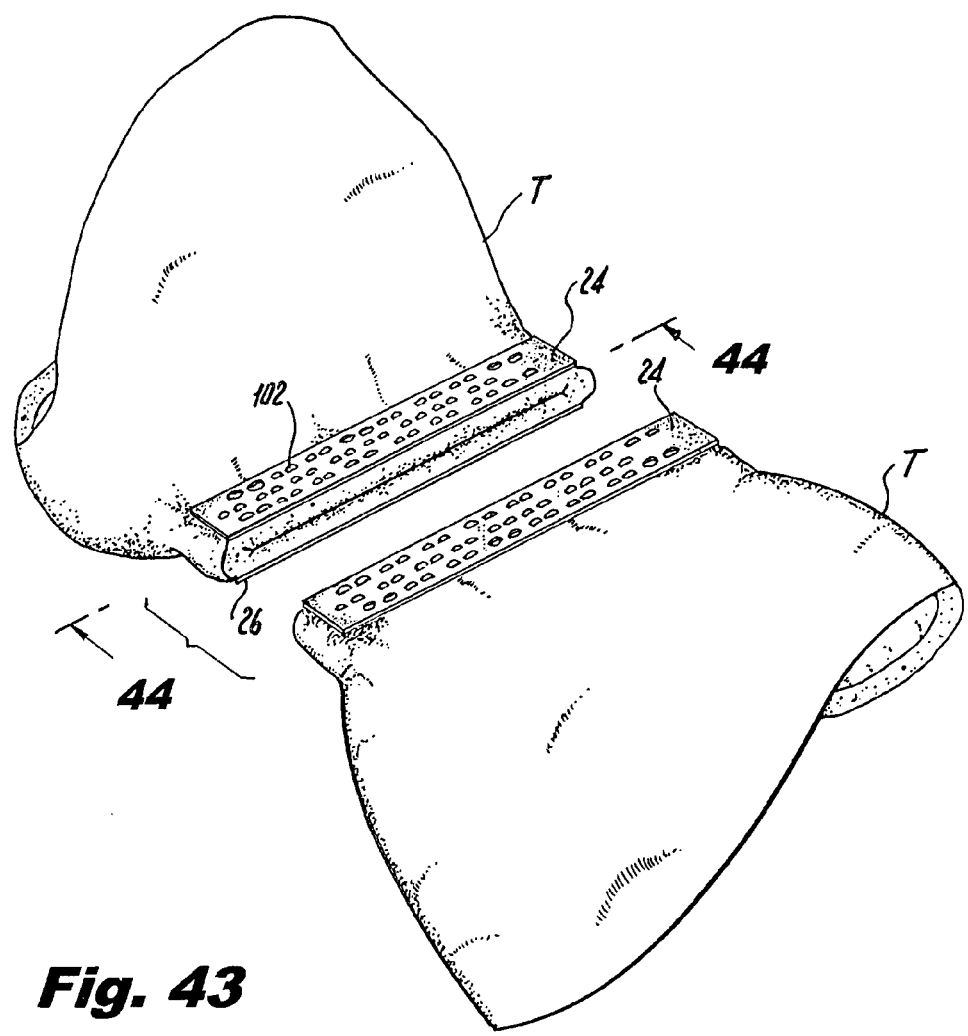
FIG. 43 is a perspective view of the stapled tissue section.
Figure 44:
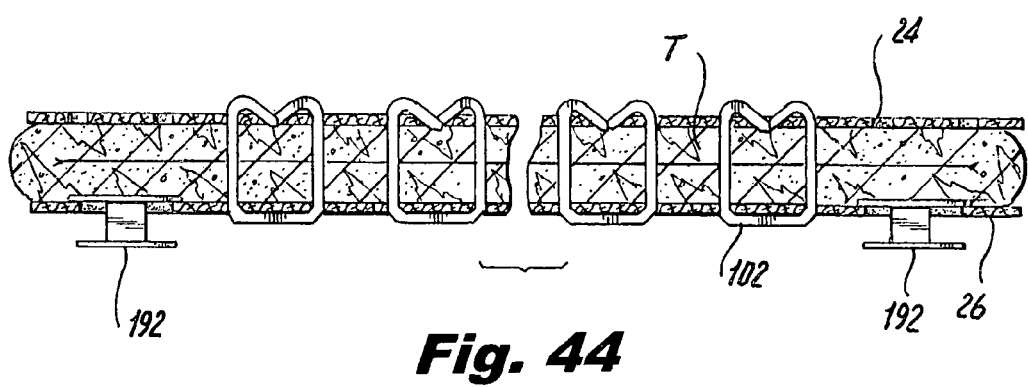
FIG. 44 is a cross-sectional view of the stapled tissue section taken along line 44-44 of FIG. 43.

The resultant tissue T, divided and stapled closed with staples 102 is shown in FIGS. 43 and 44. As shown, anvil buttress material 24 and cartridge buttress material 26 are stapled to tissue T thereby reinforcing the staple lines formed by staples 102 and sealing the tissues section T. In this manner, cartridge buttress retention system 190 allows cartridge buttress material 26 to be detachably retained on staple containing cartridge 22 and released upon stapling to tissue.

It will be understood that various modifications may be made to the embodiments disclosed herein. For example, the disclosed retainers and methods are interchangeable for use in either the staple containing cartridge or anvil. Further, the disclosed methods and retention systems are not limited to stapling apparatus but may find application in other instruments and situations requiring material to be reseably retained on the surface of a surgical instrument. Additionally, the disclosed retainers can function as both buttress material retention devices and tissue connecting devices, i.e., "tissue staples" simultaneously. Therefore, the above description should not be construed as limiting, but merely as exemplifications of particular embodiments. Those skilled in the art will envision other modifications within the scope and spirit of the claims appended hereto.

The invention claimed is:

1. A surgical stapler for deploying staples in tissue, comprising:
    a pair of jaws for engaging tissue, the pair of jaws including a staple cartridge and an anvil, at least one of the jaws defining a plurality of recesses;
    a staple line buttress material including a tissue contacting surface and a jaw contacting surface, the staple line buttress material positioned on the at least one jaw such that the jaw contacting surface abuts the jaw; and
    a plurality of buttress material retainers passing through the staple line buttress material, wherein at least a portion of each of the plurality of buttress material retainers extends transversely across the tissue contacting surface of the staple line buttress material to releasably retain the staple line buttress material on the at least one jaw, each of the plurality of buttress material retainers being disposed within a selected one of the plurality of recesses of at least one of the pair of jaws so as to releasably retain the staple line buttress material on the at least one jaw, wherein at least one of the buttress material retainers is a staple having a backspan and a pair of legs extending from the backspan.

2. The surgical stapler as recited in claim 1, wherein the plurality of recesses in the at least one jaw defines a pair of holes, the legs of the staple passing through the holes such that tips of the legs are crimped over the staple line buttress material.

3. The surgical stapler as recited in claim 1, wherein the legs of the staple are inserted through the staple line buttress material such that the legs of the staple are partially positioned within the recesses and the backspan of the staple secures the staple line buttress material to the at least one jaw.

4. The surgical stapler as recited in claim 3, wherein the legs of the staple are crimped within the recesses.

5. The surgical stapler as recited in claim 1, wherein the staple line buttress material includes a plurality of slots and the recesses are formed as slots.

6. The surgical stapler as recited in claim 1, wherein the buttress material retainer is absorbable within the body of a patient.

7. A surgical stapler for deploying staples in tissue, comprising:
    a pair of jaws for engaging tissue, the pair of jaws including a staple cartridge and an anvil, at least one of the jaws defining a plurality of recesses;
    a staple line buttress material including a tissue contacting surface and a jaw contacting surface, the staple line buttress material positioned on the at least one jaw such that the jaw contacting surface abuts the jaw, wherein the staple line buttress material includes a plurality of slots and the recesses are formed as slots; and
    a plurality of buttress material retainers passing through the staple line buttress material, wherein at least a portion of each of the plurality of buttress material retainers extends transversely across the tissue contacting surface of the staple line buttress material to releasably retain the staple line buttress material on the at least one jaw, each of the plurality of buttress material retainers being disposed within a selected one of the plurality of recesses of at least one of the pair of jaws so as to releasably retain the staple line buttress material on the at least one jaw, wherein the buttress material retainer is a clip passing through the slots in the staple line buttress material and the slots in the at least one jaw.

8. The surgical stapler as recited in claim 7, wherein the buttress material retainer is a clip having an a plate and an angled lip extending from the plate, the angled lip engaging the staple line buttress material.

9. The surgical stapler as recited in claim 8, wherein the clip has an angled edge along one side, the angled edge being engagable with a driver of the surgical stapler.

10. The surgical stapler as recited in claim 7, wherein the clip is an I-beam having a center portion and upper and lower beams extending from the center portion.

11. The surgical stapler as recited in claim 10, wherein an underside of the upper beam engages the staple line buttress material.

12. The surgical stapler as recited in claim 10, wherein ends of the lower beam frictionally engage surfaces defining the recesses.

13. The surgical stapler as recited in claim 7, wherein the buttress material retainer is absorbable within the body of a patient.

* * * * *